US010874753B2

(12) United States Patent
Driver et al.

(10) Patent No.: US 10,874,753 B2
(45) Date of Patent: Dec. 29, 2020

(54) RADIOPHARMACEUTICAL CONJUGATE OF A METABOLITE AND AN EPR AGENT, FOR TARGETING TUMOUR CELLS

(71) Applicants: The South African Nuclear Energy Corporation Limited, Brits Magisterial District (ZA); University of Cape Town, Cape Town (ZA)

(72) Inventors: Cathryn Helena Stanford Driver, Modimolle (ZA); Jan Rijn Zeevaart, Flaurana (ZA); Mohamed Iqbal Parker, Cape Town (ZA); Roger Hunter, Cape Town (ZA)

(73) Assignees: The South African Nuclear Energy Corporation Limited, Brits Magisterial District (ZA); University of Cape Town, Cape Town (ZA)

( * ) Notice: Subject to any disclaimer, the term of this patent is extended or adjusted under 35 U.S.C. 154(b) by 535 days.

(21) Appl. No.: 15/514,138

(22) PCT Filed: Sep. 25, 2015

(86) PCT No.: PCT/IB2015/057378
§ 371 (c)(1),
(2) Date: Mar. 24, 2017

(87) PCT Pub. No.: WO2016/046793
PCT Pub. Date: Mar. 31, 2016

(65) Prior Publication Data
US 2017/0296684 A1    Oct. 19, 2017

(30) Foreign Application Priority Data
Sep. 26, 2014  (GB) .................................. 1417067.4

(51) Int. Cl.
| A61K 9/00 | (2006.01) |
| A61K 51/10 | (2006.01) |
| A61K 51/04 | (2006.01) |
| A61K 51/06 | (2006.01) |
| A61K 51/08 | (2006.01) |
| A61K 51/12 | (2006.01) |

(52) U.S. Cl.
CPC ...... *A61K 51/1045* (2013.01); *A61K 51/0474* (2013.01); *A61K 51/0491* (2013.01); *A61K 51/0497* (2013.01); *A61K 51/065* (2013.01); *A61K 51/081* (2013.01); *A61K 51/088* (2013.01); *A61K 51/121* (2013.01)

(58) Field of Classification Search
CPC ................................................ A61K 51/1045
See application file for complete search history.

(56) References Cited

U.S. PATENT DOCUMENTS

| 2004/0067196 | A1 | 4/2004 | Brunke et al. |
| 2011/0059076 | A1* | 3/2011 | McDonagh ............ C07K 16/32 |
| | | | 424/133.1 |
| 2015/0231285 | A1 | 8/2015 | Wang et al. |

FOREIGN PATENT DOCUMENTS

| EP | 0205326 | 12/1986 |
| EP | 0233619 | 8/1987 |
| JP | H5-239039 A | 9/1993 |
| WO | 87/05031 | 8/1987 |
| WO | 94/17829 | 8/1994 |
| WO | 02/087498 | 11/2002 |
| WO | 02087498 A2 | 11/2002 |
| WO | 03/011345 | 2/2003 |
| WO | 2004062574 | 7/2004 |
| WO | 2007064661 | 6/2007 |
| WO | 2007/121453 | 10/2007 |
| WO | 2007120153 | 10/2007 |
| WO | 2008045604 | 4/2008 |
| WO | 2008105773 | 9/2008 |
| WO | 2008/134586 | 11/2008 |
| WO | 2010/062557 | 6/2010 |
| WO | 2010062381 | 6/2010 |
| WO | 2010063069 | 6/2010 |
| WO | 2011008985 | 1/2011 |
| WO | 2011008992 A2 | 1/2011 |
| WO | 2012/063028 | 5/2012 |
| WO | 2013127885 | 9/2013 |

OTHER PUBLICATIONS

Bagi, "Targeting of therapeutic agents to bone to treat metastatic cancer", Adv. Drug Deliv. Rev., 2005, 57, 995-1010.
Benoist, et al., "A Click procedure with heterogeneous copper to tether technetium-99m chelating agents and rhenium complexes—Evaluation of the chelating properties and biodistribution of the new radiolabelled glucose conjugates", Carbohydrate Research, 2011, 346, 25-34.
Branco de Barros, et al., "A novel D-glucose derivative radiolabeled with technetium-99m : Synthesis. biodistribution studies and scintigraphic images in an experimental model of Ehrlich tumor", Bioorg. Med. Chem. Lett., 2010, 20, 2478-2480.
(Continued)

*Primary Examiner* — Paul W Dickinson
(74) *Attorney, Agent, or Firm* — Meunier Carlin & Curfman LLC

(57) ABSTRACT

This invention relates new radiopharmaceutical conjugates for use in improved methods of diagnosis and treatment of cancer. The radiopharmaceutical conjugate comprises, in sequence: a metabolite that targets tumour cells, bound to a chelating agent capable of containing a radionuclide, bound to a linker capable of binding with an EPR agent in vitro or in vivo; or a chelating agent capable of containing a radionuclide, bound to a metabolite that targets tumour cells, bound to a linker capable of binding with an EPR agent in vitro or in vivo. The radiopharmaceutical conjugates of the present invention provide active and passive targeted radio nuclide delivery systems that can help to improve the biodistribution and pharmacological toxicity of the radiopharmaceuticals used for the diagnosis and therapy of cancer.

24 Claims, 2 Drawing Sheets

Specification includes a Sequence Listing.

(56) References Cited

OTHER PUBLICATIONS

Capello, et al., "Peptide Receptor Radionuclide Therapy in Vitro Using [111In-DTPA0]Octreotide", J. Nucl. Med. 2003, 44, 98-104.
Carlsson, et al., "Tumor therapy with radionuclides: Assesment of progress and problems", Radiother. Oncol. 2003, 66, 107-117.
Chaumet-Riffaud, et al., "Synthesis and application of lactosylated, (99m)Tc chelating albumin for measurement of liver function", Bioconjugate Chem. 2010, 2, 589-595.
Chen, et al., "Synthesis and biological evaluation of technetium-99m-labeled deoxyglucose derivatives as imaging agents for tumor", Bioorg. Med. Chemistry Lett. 2006, 16, 5503-5506.
Driver, et al., "The Development of a Gluco-Albumin Macromolecule as a Specific Targeting Agent for Tumors", Oral Presentation. SANHARP conference in 2011 held at Ithemba LABS on Oct. 12-14, 2011, 2 pages.
Driver, et al., "The Development of a Specific Tumour Targeting Agent as a Potential Radiopharmaceutical Therapeutic", BOCC-2013 Organic Chemistry Conference in Tutzing, Germany Sep. 29-Oct. 4, 2013, abstract and poster, 1 page.
Elzoghby, et al., "Albumin-based naoparticles as potential controlled release drug delivery systems", Journal of Controlled Release. 2012, 157, 168-182.
Fincha, et al., "Synthesis of Target-Specific Radiolabelled Peptides for Diagnostic Imaging", Bioconjugate Chem. 2003, 14, 3-17.
Garoufis, et al., "Palladium coordination compounds as antiviral, anti-fungal, anti-microbial and anti-tumor agents", Coordination Chemistry Reviews, 2009, 253, 1384-1397.
Gilman, et al., "State-of-the-Art FDG-PET Imaging of Lung Cancar", Seminars in Roentgen. 2005, 40, 143-153.
Ginj, et al., "Trifunctional Somatostatin-Based Derivatives Designed for Targeted Radiotherapy Using Auger Electron Emitters", J. Nud. Med. 2005, 46, 2097-2103.
Hamdy, et al., "The Palliative Management of Skeletal Metastases in Prostate Cancer", Use of Bone-Seeking Radionuclides and Bispjosphonates; Semin. Nucl. Med. 2001, 62-68.
Hamoudeh, et al., "Radionuclides delivery systems for nuclear imaging and radiotherapy of cancer", Adv. Drug Deliv. Rev., 2008, 60, 1329-1346.
Iyer, et al., "Exprfoiting the enhanced permeability and retention effect for tumor targeting", Drug. Discov. Today, 2006, 11, 812-818.
Kassis, "Therapeutic Radionuclides: Biophysical and Radiobiologic Principles", Semin. Nucl. Med. 2008, 38, 358-366.
Kratz, "Albumin as a drug carrier: Design of prodrugs, drug conjugates and nanoparticles", J. Con. Rel. 2008, 132, 171-183.
Larpent, et al., "Macrocyclic Sugar-Based Surfactants: Block Molecules Combining Self-Aggregation and Complexation Properties", Angew. Chem. Int. Ed., 2004, 43, 3163 -3167.
Liang, et al., "Cyclam complexes and their applications in medicine", Chem. Soc. Rev., 2004,33,246-266.
Maeda, et al., "Polymeric drugs for efficient tumor-targeted drug delivery based on EPR-effect", Eur. J. Pharm. Biopham. 2009, 71, 409-419.
Mayosi, et al., "The burden of non-communicable diseases in South Africa", The Lancet 2009, 374, 934-947.
Miele, et al., "Albumin-bound formulation of paclitaxel (Abraxane® ABI-007) in the treatment of breast cancer", International Journal of Nanomedicine, 2009, 4, 99-105.
Milenic, et al., "Antibody-targeted radiation cancer therapy", Nat. Rev. Drug Disc. 2004, 3, 488-499.
Ramogida, et al., "Tumour targeting with radiometals for diagnosis and therapy", Chem. Commun. 2013, 49, 4720-4739.
Rooyen, et al., "A possible in vivo generator Pd / 103m Rh—Recoil considerations", Applied Radiation and Isotopes, 2008, 66,1346-1349.
Saito, et al., "Drug delivery strategy utilizing conjugation via reversible disulfide linkages: role and site of cellular reducing activities", Advanced Drug Delivery Reviews. 2003, 55, 199-215.
Sinha, et al., "Nanotechnology in cancer therapeutics: bioconjugated nanoparticles for drug delivery", Mol. Cancer. Ther. 2006, 5, 1909-1917.
Srivastava, et al., "Recent advances in Radionuclide Therapy", Semin. Nucl. Med. 2001, 330-341.
Stokkel, et al., "The role of FDG-PET in the clinical management of head and neck cancer", Oral Oncol. 1998, 34, 466-471.
Ting, et al., "Nanotargeted Radionuclides for Cancer Nuclear Imaging and Internal Radiotherapy", Journal of Biomedicine and Biotechnology. 2010, Article ID 953537, 17 pages.
Tolmachev, et al., "Evaluation of a Maleimido Derivative of NOTA for Site-Specific Labeling of Affibody Molecules", Bioconjugate Chem. 2011, 22, 894-902.
Waldmann, "Monoclonal antibodies in diagnosis and therapy", Science 1991, 252, 1657-1662.
Xu, et al., "Targeted Albumin-Based Nanoparticles for Delivery of Amphipathic Drugs", Bioconjugate Chem. 2011, 22, 870-878.
Yang, et al., "Imaging with 99mTc ECDG Targeted at the Multifunctional Glucose Transport System: Feasibility Study with Rodents1", Radiology 2003, 226, 465-437.
Zoller, et al., "Endoradiotherapy in cancer treatment—Basic concepts and future trends", European Journal of Pharmacology. 2009, 20(3),625, 55-62.
Hosseinkahani, H. et al. "Liver targeting of plasmid DNA by pullulan conjugation based on metal coordination", Journal of Controlled Release 83 (2002) pp. 287-302.
Mao, Y. et al. "The Preparation of 99mTcm-GSA and Its Instant Lyophilized Kit for Hepatic Receptor Imaging", Journal of Isotopes, vol. 21, No. 2, May 2008, pp. 88-94.
Muller, C. et al. "DOTA Conjugate with an Albumin-Binding Entity Enables the First Folic Acid-Targeted 177Lu-Radionuclide Tumor Therapy in Mice", The Journal of Nuclear Medicine, vol. 54, No, 1, Jan. 2013, pp. 124-131.
International Search Report dated Apr. 25, 2016, from International Application No. PCT/IB2015/057378, 11 pages.
Mao et al., The Preparation of 99TcM-GSA and Its Instant Lyophilized Kit for Heptic Receptor Imaging. Journal of Isotopes vol. 21, 2008, pp. 88-94, 2008, English Abstract.
Chen et al., Pegylated Arg-Gly-Asp Peptide: 64 Cu Labeling and PET Imaging of Brain Tumor AlphavBeta3-Integrin Expression, The Journal of Nuclear Medicine, vol. 45, No. 10, pp. 1776-1783, 2004.
Antczak et al., Influence of the linker on the biodistribution and catabolism of actinium-225 self-immolative tumor-targeted isotope generators. Bioconjug Chem, vol. 17(6), pp. 1551-1560, 2006.
Kumaresan et al., On-Demand Cleavable Linkers for Radioimmunotherapy. In: Bugge T., Antalis T. (eds) Proteases and Cancer. Methods in Molecular Biologytm (Methods and Protocols), vol. 539. Humana Press, pp. 191-211, 2009.
Hartmann et al., Selecting an Intervention Time for Intravascular Enzymatic Cleavage of Peptide Linkers to Clear Radioisotope from Normal Tissues. Cancer Biotherapy and Radiopharmaceuticals, vol. 22(4), pp. 556-563, 2007.
Kukis et al., Cleavable Linkers to Enhance Selectivity of Antibody-Targeted Therapy of Cancer. Cancer Biotherapy & Radiopharmaceuticals, vol. 16(6), pp. 457-467, 2001.
Ogbomo et al., 177Lu-labeled HPMA copolymers utilizing cathepsin B and S cleavable linkers: synthesis, characterization and preliminary in vivo investigation in a pancreatic cancer model. Nucl Med Biol., vol. 40(5), pp. 606-617, 2013.

* cited by examiner

SEQUENCE LISTING

```
<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Gly Gly Gly Phe
1

<210> SEQ ID NO 2
<211> LENGTH: 4
<212> TYPE: PRT
<213> ORGANISM: Homo sapiens

<400> SEQUENCE: 2

Gly Phe Leu Gly
1

<210> SEQ ID NO 3
```

```
<211> LENGTH: 4
<212> TYPE: PRT
<213> ORGANISM: Homo sapiens

<400> SEQUENCE: 3

Ala Leu Ala Leu
1

<210> SEQ ID NO 4
<211> LENGTH: 5
<212> TYPE: PRT
<213> ORGANISM: Homo sapiens

<400> SEQUENCE: 4

Pro Met Gly Leu Pro
1               5

<210> SEQ ID NO 5
<211> LENGTH: 8
<212> TYPE: PRT
<213> ORGANISM: Homo sapiens

<400> SEQUENCE: 5

Gly Pro Leu Gly Ile Ala Gly Gln
1               5
```

RADIOPHARMACEUTICAL CONJUGATE OF A METABOLITE AND AN EPR AGENT, FOR TARGETING TUMOUR CELLS

BACKGROUND OF THE INVENTION

THIS invention relates to new radiopharmaceutical conjugates for use in improved methods of diagnosis and treatment of cancer.

Cancer is defined as a neoplastic (new growth) disease in which there is uncontrolled growth of abnormal cells resulting in the formation of a cellular mass known as a tumour. In most cases, if left untreated, the growth of the tumour eventually leads to the organism's death. Cancer cells are often malignant which results in the dissemination of the altered cells through the lymphatic and vascular system producing growth of tumours in other parts of the body.

Once cancer has been diagnosed, the general forms of treatment include surgery, chemotherapy or radiation therapy. Most often a combination of the three is applied.

Surgery is an invasive procedure whereby physical intervention on tissues is performed by cutting into the patient's body. The surgery is then followed up with chemotherapy or radiation Chemotherapy is the administration of synthetic anti-cancer drugs to patients in order to kill cancerous cells. A large number of chemotherapeutic drugs exist with a variety of mechanisms of action that generally result in the inhibition of DNA synthesis and replication or inhibition of cellular mitosis which then leads to induction of cellular apoptosis. While these chemotherapeutic drugs are relatively effective in treating a number of different types of cancer, the major challenge with using them more consistently and for a longer period is the large number of side effects that occur during treatment. The side effects range from nausea, vomiting, hair loss, loss of appetite, mouth ulcers, decrease in blood cell count and many other more serious effects. These effects are as a result of the administered drug not only affecting the cancer cells but being spread throughout the body and also damaging or killing normal, healthy cells.

Conventional radiation therapy is the use of high-energy radiation such as X-rays, gamma rays and charged particles to kill tumour cells. The cells are destroyed when the radiation irreversibly damages DNA either directly or by generating charged particles such as reactive oxygen species. Irradiation of the tumour site is done by means of a machine for external-beam radiation therapy or by means of a radioactive material seed placed within the tumour for internal radiation therapy. Radiation therapy is a viable source of cancer treatment, especially in combination with surgery and chemotherapy but it is also not without its challenges. Besides the fact that radiation also does damage to surrounding healthy tissue, another challenge is that radiation is not very effective in low oxygen (hypoxic) conditions found in solid tumour environments. Decreased radiosensitivity will then lead to local recurrence of the tumour and lower rates of overall patient survival.

The current treatment strategies for cancer have had success in putting a large percentage of patients into remission. However, a great percentage of people diagnosed with cancer unfortunately do not survive and all patients receiving treatment have varying degrees of very unpleasant, adverse side effects.

It is an object of this invention to provide new radiopharmaceutical conjugates for use in improved methods of diagnosis and treatment of cancer.

SUMMARY OF THE INVENTION

A bioconjugate according to the present invention comprises a metabolite that targets tumour cells, a chelating agent capable of containing a radionuclide, and an EPR agent, wherein the EPR agent is bound to the bioconjugate by a cleavable linker.

The invention also covers a proconjugate comprising a metabolite that targets tumour cells, a chelating agent capable of containing a radionuclide, and a cleavable linker capable of binding with an EPR agent in vitro or in vivo.

In a preferred embodiment of the invention, the bioconjugate is a linear molecule comprising, in sequence:
a metabolite that targets tumour cells, bound to a chelating agent capable of containing a radionuclide, bound to a linker, preferably a cleavable linker, which is bound to an EPR agent.

In a preferred embodiment of the invention, the proconjugate is a linear molecule comprising, in sequence:
a metabolite that targets tumour cells, bound to a chelating agent capable of containing a radionuclide, bound to a linker, preferably a cleavable linker, capable of binding with an EPR agent in vitro or in vivo.

A "linker" comprises a carbon chain of a suitable length (4 to 20, typically 8 to 15 carbon atoms) that connects the chelating agent to the EPR agent. The linker may be non-cleavable, but is preferably a cleavable linker. A cleavable linker contains a cleavable bond that is cleaved in vivo within a tumour environment, for example: by an acidic pH (pH less than 7, typically about 4 to 6), by glutathione (which is present in high levels in the tumour environment), or where there is up-regulation of enzymes such as matrix proteases; and release the metabolite and chelating agent from the EPR agent to allow for cellular internalization of the metabolite and chelating agent. Examples of non-cleavable linkers are linkers that are connected through amide, thiourea, thioether or triazole bonds. Examples of cleavable linkers are linkers that contain hydrazine, or disulfide bonds, or enzymatically cleavable peptide sequences.

By "EPR agent" is meant: a molecule with a size greater than 40 kDa such as polymeric nanoparticles, polymeric micelles, dendrimers, liposomes, viral nanoparticles, carbon nanoparticles and proteins such as albumin or heparin that accumulates in a tumour due to the Enhanced Permeability and Retention (EPR) effect.

The EPR agent may be a synthetic polymer that is biodegradable such as polyglutamate (PG), polylactide (PLA) and poly(D,L-lactide-co-glycolide)(PLGA), a synthetic polymer that is biocompatible but not biodegradable such as Polyethylene glycol (PEG) and N-(2-hydroxypropyl)methylacrylamide (HMPA), or a natural polymer such as albumin, chitosan and heparin.

By "metabolite that targets tumour cells" is meant: a molecule such as monoclonal antibodies, proteins and peptides and small molecules (i.e. molecules that are smaller than 1000 Da in size (generally 100 to 700 Da) that are in vivo recognized by up-regulated receptors, antigens or other proteins on the cancer-cell surface. The metabolite may be an agonist or an antagonist.

Examples of suitable monoclonal antibodies (mAb) are 2C5, Gemtuzumab, Rituximab, Cetuximab, Bevacizumab, Pertuzumab and PSMA Ab antibody.

Examples of proteins and peptides are Transferrin, RGD peptides, Octreotide, Bombesin, and VIP.

Examples of small molecules are folate, mannose, glucose and galactose.

By "chelating agent" is meant a bifunctional chelating agent (BFCA) which is a compound consisting of a varied number of heteroatoms, generally O, N or S that are able to complex a radioisotope. The chelating agent may be cyclic or acylic, preferably cyclic.

Examples of cyclic chelators are: 1,4,7-Triazacyclononane (TACN); 1,4,7-triazacyclononane-triacetic acid (NOTA); 1,4,7-triazacyclononane-N-succinic acid-N',N''-diacetic acid(NOTASA); 1,4,7-triazacyclononane-N-glutamic acid-N',N''-diacetic acid(NODAGA); 1,4,7-triazacyclononane-N,N',N''-tris (methylenephosphonic)(NOTP); 1,4,7,10-tetraazacyclododecane ([12]aneN4)(cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri (methanephosphonic acid) (DOSP); 1,4,7,10-tetraazacyclodecane-1-glutamic acid-4,7,10-triacetic acid (DOTAGA); 1,4,7,10-tetraazacyclodecane-1-succinic acid-4,7,10-triacetic acid(DOTASA); 1,4,8,11-tetraazacyclotetradecane ([14]aneN4)(cyclam); 1,4,8,12-tetraazacyclopentadecane ([15]aneN4); 1,5,9,13-tetraazacyclohexadecane ([16] aneN4); 1,4-ethano-1,4,8,11-tetraazacyclo-tetradecane (et-cyclam); 1,4,8,11-15-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis(carboxymethyl)-1,4,8,11-tetraazabicyclo[6.6.2]-hexadecane(CB-TE2A); 3,6,10,13,16,19-hexaazabicyclo [6.6.6]icosane(Sar); phthalocyanines and their derivatives; porphyrins and their derivatives.

Examples of acyclic chelators are: ethylene-diamine-tetraacetic-acid (EDTA); and diethylene-triamine-penta-acetic acid (DTPA). S-acetylmercaptosuccinic anhydride (SAMSA); (2-mercaptoethyl)(2-((2-mercaptoethyl)amino) ethyl)-carbamic acid(N2S2-DADT); 1,1'-(ethane-1,2-diyl-bis(azanediyl))bis(2-methylpropane-2-thiol)(N2S2 BAT-TM), (2-(2-mercaptoacetamido)ethyl)-cysteine (N2S2-MAMA); 2,3-bis(2-mercaptoacetamido)-propanoic acid (N2S2 DADS); ethylenedicysteine (EC); 2,2',2''-nitrilotri-ethanethiol (NS3); 2-ethylthio-N,N-bis(pyridin-2-yl) methyl-ethanamine (N3S); ((2-mercaptoacetyl) glycylglycyl)carbamic acid (MAG$_3$) and 4-(2-(2-(2-mercaptoacetamido)acetamido)-acetamido)butanoic acid (MAG$_2$-GABA); (1,2-bis{[[6-(carboxy)pyridine-2-yl] methyl]-amino}-ethane) (H$_2$dedpa); Nitrilotris(methylenephosphonic acid) (NTMP); ethylenediaminetetramethylene-phosphonic acid (EDTMP), diethylenetriaminepenta-methylene phosphonic acid (DTPMP); Hydrazinonicotinic acid (HYNIC); N'-{5-[Acetyl(hydroxy)amino]-pentyl}-N-[5-({4-[(5-aminopentyl)-(hydroxy)amino]-4-oxobutanoyl}amino)pentyl]-N-hydroxysuccin-amide (Deferoxamine).

Examples of radionuclides that may be used for imaging (diagnosis) include: $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{16}$F, $^{123}$I.

Examples of radionuclides that may be used for therapeutic purposes include: $^{188}$Re, $^{186}$Re, $^{153}$Sm, $^{166}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{199}$Au, $^{195m}$Pt, $^{193m}$Pt, $^{197}$Pt, $^{117m}$Sn, $^{103}$Pd, $^{103m}$Rh, $^{177}$Lu, $^{223}$Ra, $^{224}$Ra, $^{227}$Th, $^{32}$P, $^{161}$Tb and $^{33}$P, $^{125}$I, $^{203}$Pb, $^{201}$Ti, $^{119}$Sb, $^{58m}$Co, $^{161}$Ho.

Preferred radionuclides are Auger electron emitting radionuclides. These are radionuclides that emit Auger electrons which are very low energy (<500 eV) electrons with a very short, nanometer range that are emitted from the outer shell of a decaying atom during the rearrangement of the electron shells due to electron capture or internal electron conversion processes. Such radionuclides include $^{111}$In, $^{203}$Pb, $^{201}$Ti, $^{103}$Pd, $^{103m}$Rh, $^{119}$Sb, $^{58m}$Co, $^{161}$Ho, $^{161}$Tb, $^{61}$Cu, $^{67}$Cu, $^{195m}$Pt, $^{193m}$Pt, $^{117m}$Sn.

The invention also covers a bioconjugate or proconjugate defined above, with the chelating agent containing the radionuclide.

Further aspects of the invention include modification of the EPR agent for attachment to the linker and modification of the metabolite for attachment to the chelating agent; as well as modification of the linker and chelating agent.

A radiopharmaceutical bioconjugate in accordance with an embodiment of the invention is produced by joining three synthetic components:
1) a metabolite that targets tumour cells, preferably a glucose containing linker that is functionalised for connection to the chelating agent through alkylation or acylation;
2) a chelating agent, preferably a cyclam functionalised through N-linkages for radioisotope chelation; and
3) a linker, preferably a linker functionalised with maleimide for attachment to EPR agent to form a proconjugate before linking to:
4) biomolecule/EPR agent, preferably albumin.

A preferred radionuclide is $^{103}$Pd.

Conditions for a method for the synthesis of the proconjugate:
the functionalization of the metabolite requires that suitable protection strategies for reactive groups within the metabolite be carried out. The metabolite is then reacted with an alkyl halide chain to form a metabolite connected to a carbon chain with a suitable terminal functional group that is then converted into a halide or an acid chloride;
the functionalization of the non-cleavable linker requires that an alkyl chain of suitable length with suitable functional groups for substitution be converted into a linker with an alkyl halide at one end for attachment to the chelating agent and a protected amine at the other end. The functionalization of the cleavable linker requires that two suitable fragments with suitable terminal functional groups be connected through a bond that can be cleaved; example a disulfide bond: the first fragment containing an alkyl halide at one end for attachment to the chelating agent and a thiotosylate at the other terminus and the second fragment with a protected amine at the distal end to the chelating agent and a thiol group at the proximal end;
the functionalization of the chelator requires that the chelator is first mono-alkylated with the linker through an $S_N2$ reaction and then alkylated a second time with the metabolite though an $S_N2$ or $S_N$Ac reaction. The remaining amines of the macrocycle are then reacted with suitable acetate groups that will assist in metal complexation. A deprotection strategy of all protected functional groups is then carried out. The terminal amine is then converted into a functional group such as maleimide to bind to the EPR agent.

Radiolabelling is carried out by dissolving the pro-conjugate in water. To the pro-conjugate is added anaqueous solution of the radioisotope to effect radiolabeling.

Formulations containing the bioconjugates and proconjugates described above may comprise these bioconjugates or proconjugates that have already been radiolabelled or not, in an aqueous solution. If a specific pro-conjugate is not water soluble then small amounts of ethanol or dimethylsulfoxide can be used at such levels that are not toxic to the cells. Complexation to a radioisotope may be done in kit form which includes a sealed container with a predetermined amount of pro- or bioconjugate as well as a reducing agent if necessary for labeling to which is added the radioisotope in an aqueous solution. The kits may also contain pharmaceutical adjunct material such as pharmaceutical grade salts for osmotic pressure, buffers, preservatives, anti-oxidants and such. The components of the kit may be in liquid, frozen or dry form.

Methods of diagnosis and therapeutic treatment require the administration of the radiolabelled conjugates as an intravenous or intraperitoneal dose in sterile saline or plasma. The unit dose to be administered has a radioactivity of about 0.01-300 mCi and the solution injected with this dose is 0.1-10 mL.

DESCRIPTION OF THE INVENTION

Figure 1:
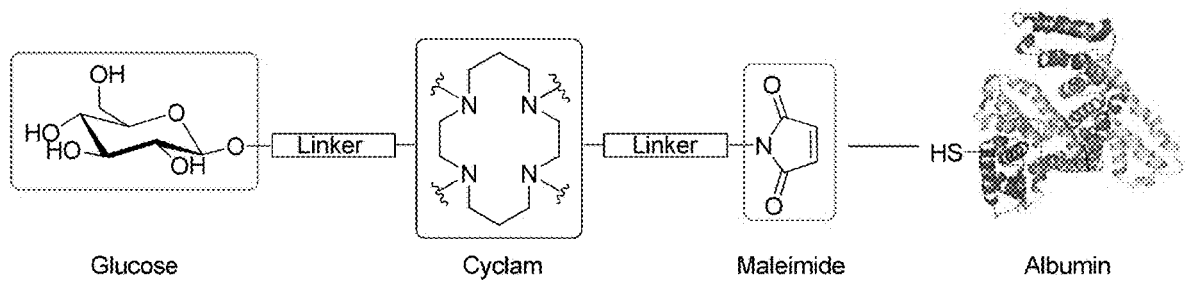
FIG. 1 depicts an illustration of a radiopharmaceutical bioconjugate.
Figure 2A:
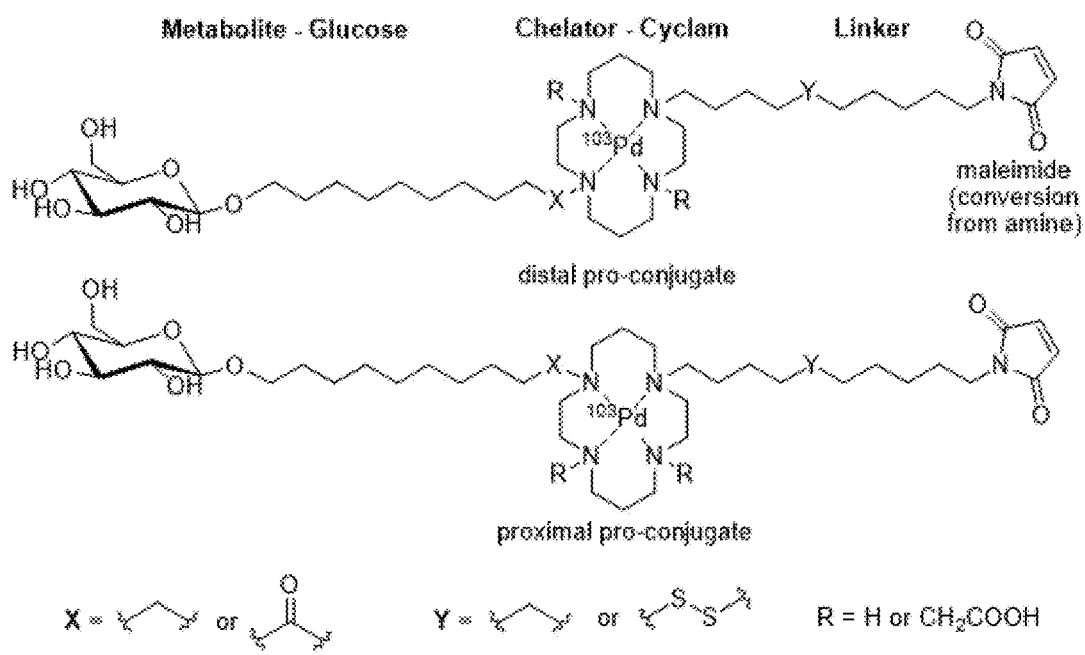
FIG. 2A depicts two proposed synthetic glucose-cyclam-maleimide pro-conjugates with various linker alternatives that are radiolabelled with $^{103}$Pd.
Figure 2B:
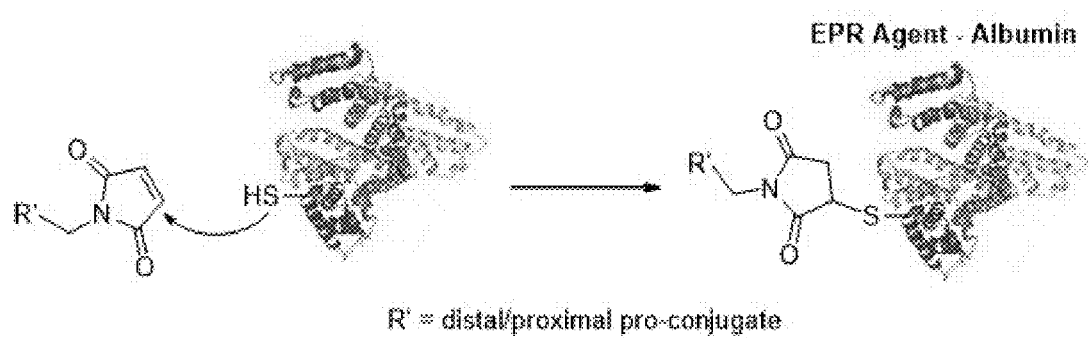
FIG. 2B depicts Michael addition of the free thiol in albumin to the maleimide of the pro-conjugates to form the radiopharmaceutical bioconjugate.

The present invention relates to new radiopharmaceutical conjugates for targeted cancer therapies by more efficient and accurate delivery systems in order to increase the efficacy of the cancer drug by improving the pharmacokinetics and bioavailability of the drugs and thereby decreasing the drugs side effects.

Passive targeting is the selective accumulation of certain therapeutic macromolecules within the tumour due to unique anatomical and pathophysiological abnormalities of the tumour vasculature. These abnormalities include hypervasculature with defective blood vessel architecture and poor lymphatic drainage and together they have become known as the EPR effect.

Active targeting is the site-specific targeting of cell-surface molecules and receptors on cancer cells in which the efficiency of the active targeting agent will depend on the receptor being targeted. Ideally, the cell receptors or surface antigens that are targeted would be exclusively and homogenously expressed on the cancer cells and would not be released into the blood stream. It is also necessary to ensure that the targeting agent selected, once bound to the surface, will be internalised into the cell, generally through receptor-mediated endocytosis.

Thus, the development and use of drugs that are designed to exploit the tumour microenvironment and EPR effect to accumulate within the tumour is known as passive targeting while drugs that are developed to have a high affinity for one of the upregulated cell receptors and so increase their accumulation within the tumour cell is known as active targeting.

Radiopharmaceuticals fall under the category of nuclear medicine. Diagnostic radiopharmaceuticals produce radiation emissions which are recorded externally to image the localisation site. The use of radiopharmaceuticals for treatment can therefore be classified as a form of endoradiotherapy as they deliver a radiation dose internally to the site of the affected tissue and the emissions destroy the surrounding cells. Tumour imaging agents are used in the range of 10-1000 nm and should not have any pharmacological effect while therapeutic agents have an effect based on the damage done by the ionizing radiation and are so used in a slightly higher concentration than imaging agents but still in much smaller amounts than a chemotherapeutic agent.

Radiopharmaceuticals are generally made up of two components, a radionuclide and a carrier, and it is these two aspects that determine the function and efficiency of the radiopharmaceutical for imaging or therapy. The aim of a radiopharmaceutical is to deliver the radionuclide quantitatively to the tumour site without any radiation damage to healthy tissue. As such, the design of a radiopharmaceutical requires careful consideration of the physical decay properties of the radioisotope used, the specific in vivo targeting of the tumour and the clearance of the compound from other tissues. Radiopharmaceutical localisation through receptor binding is described as active targeting whereas localisation though tumour inherent properties and the EPR-effect are described as passive targeting as previously discussed. Active and passive targeted radionuclide delivery systems can help to improve the biodistribution and pharmacological toxicity of the radiopharmaceuticals used for the diagnosis and therapy of cancer.

The radiopharmaceutical conjugates of the present invention are constructed to achieve targeted cancer therapies by making use of "passive" targeting and the enhanced permeability and retention (EPR), and "active" (receptor-mediated) targeting.

A radiopharmaceutical bioconjugate according to the present invention comprises a metabolite that targets tumour cells, a chelating agent capable of containing a radionuclide, and an EPR agent, wherein the EPR agent is bound to the bioconjugate by a linker.

The invention also covers a radiopharmaceutical proconjugate comprising a metabolite that targets tumour cells, a chelating agent capable of containing a radionuclide, and a cleavable linker capable of binding with an EPR agent in vitro or in vivo.

In a preferred embodiment of the invention, the bioconjugate is a linear molecule comprising, in sequence:
  a metabolite that targets tumour cells, bound to a chelating agent capable of containing a radionuclide, bound to a linker, preferably a cleavable linker, which is bound to an EPR agent.

In a preferred embodiment of the invention, the proconjugate is a linear molecule comprising, in sequence:
  a metabolite that targets tumour cells, bound to a chelating agent capable of containing a radionuclide, bound to a linker capable of binding with an EPR agent in vitro or in vivo.

The "EPR agent" includes molecules such as polymer nanoparticles, polymeric micelles, dendrimers, liposomes, viral nanoparticles, carbon nanoparticles and some proteins.

Polymers are biodegradable macromolecules synthesised from repeating monomeric subunits that are biocompatible and can be either synthetic or natural. Polymer-drug conjugates are formed either by covalently bonding the drug to the polymer backbone or by encapsulating the aqueous phase drug within polymer nanoparticles. In order to obtain an efficient polymer-drug delivery system, the polymer needs to be non-toxic, have a decent drug loading capability and be stable in transit through the body but also able to release the drug at the desired location. Examples of synthetic polymers that are biodegradable include polyglutamate (PG), polylactide (PLA) and poly(D,L-lactide-co-glycolide)(PLGA). Examples of synthetic polymers that are biocompatible but not biodegradable include Polyethylene glycol (PEG) and N-(2-hydroxypropyl)methylacrylamide (HMPA). Natural polymeric proteins that can be used are albumin, chitosan and heparin. Albumin is a 66.5 kDa protein that occurs naturally in serum and has been conjugated covalently to drugs as well as being formulated into a nanoparticle that encapsulates the drug.

Polymeric micelles are formed by amphiphilic block copolymers and result in a hydrophobic core encapsulating the drug and a hydrophilic shell which renders the micelles water soluble.

Dendrimers are polymers formed from branched monomers radiating out from a central core and are able to conjugate a number of different molecules or drugs simultaneously.

Liposomes are spherical phospholipid bilayers of around 400 nm that are formed spontaneously by the self-association of phospholipids into bilayers in an aqueous environment. Drugs are loaded into the liposomes in various ways which include the assembly of the liposomes in a drug saturated aqueous environment or by means of an organic solvent exchange mechanism.

Viral nanoparticles that form a protein cage and carbon nanoparticles with surface modifications to improve solubility and bind drugs are other nanoparticles that have been used for passive targeting and drug delivery. An example is cowpea mosaic virus (CPMV).

Since the EPR effect is based on extravasation of compounds from blood vessels into the tumour environment, there are a number of vascular mediators that can affect this phenomenon and can so be used in one way or another to enhance the uptake or targeting of the drug to the tumour site. These vascular mediators include vascular endothelial growth factor (VEGF), bradykinin, nitric oxide and peroxynitrite, prostaglandins, matrix metalloproteinases and angiotensin converting enzyme (ACE) inhibitors. VEGF is an upregulated angiogenesis factor involved in blood vessel formation and tumour growth and a number of inhibitors of VEGF have been developed. Bradykinin (a vascular dilating peptide), nitric oxide, peroxynitrite and prostaglandins all play an important role in vascular permeability and extravasation and it was noted that addition of these mediators upon administration of a dye/albumin complex resulted in increased uptake of the dye into the tumour. Matrix metalloproteinases are enzymes involved with tumour invasion, metastasis and angiogenesis, and their activation by peroxynitrite facilitates the EPR effect by disintegration of the extracellular matrix as well as leading to the production of bradykinin. ACE (angiotensin converting enzyme) inhibitors prevent the conversion of angiotensin (AT)-I to AT-II which then inhibits the degradation of bradykinin leading to increased vascular permeability.

A "metabolite that targets tumour cells" is a molecule such as monoclonal antibodies, proteins and peptides and small molecules (i.e. molecules that are smaller than 1000 Da in size (generally 100 to 700 Da) that is recognized by up-regulated receptors, antigens or other proteins on the cancer-cell surface. The metabolite may be an agonist or an antagonist.

Antibodies are Y-shaped glycoproteins of high molecular weight that bind to a foreign target on the cell and inhibit pathways which result in cell death. Examples of suitable monoclonal antibodies (mAb) are 2C5, Gemtuzumab, Rituximab, Cetuximab, Bevacizumab, Pertuzumab and PSMA AntibodyAb. Trastuzumab is a mAb against HER-2/neu receptors found to be over expressed in a percentage of breast cancer patients. VEGF and epidermal growth factor (EGF) are both involved with tumour growth and angiogenesis, and their receptors (VEGFR and EGFR) are the focus of a number of mAb therapies. Cetuximab acts against EGFR whilst Bevacizumab binds to VEGFR. Despite the abundance of mAbs, in reality their use has been limited due to poor tumour accumulation (<0.01%), cross reactivity and slow blood clearance in vivo. The initial direct conjugation of a drug to a mAb met with limited success due to the possibility of only a limited number of drug molecules being attached to the mAb simultaneously. This challenge was then addressed by attaching the mAbs to the surface of a nanoparticle and loading the drug within the nanoparticle.

Proteins and peptides provide an alternative targeting strategy. Examples of proteins and peptides are Transferrin, RGD peptides, Octreotide, Bombesin, and VIP. Transferrin (Tf) is naturally occurring protein that binds iron in the blood and transports it into the cells by attachment to the transferrin-receptor. Peptides are sequences of amino acids that have improved stability and resistance to degradation due to their smaller molecular size. Examples of peptides are arginine (R), glycine (G), aspartic acid (D) (RGD) sequence which binds to the over expressed, pro-angiogenic receptor $\alpha v \beta 3$ integrin. Other peptides that have been used include octreotide which is a synthetic analogue of the naturally occurring neuropeptide somatostatin (SST) and has a high affinity for the SST receptor. Bombesin is a peptide analogue of gastrin-releasing hormone peptide (GRP) that binds to GRP receptors on a number of cancers, while vasoactive intestinal peptide (VIP) binds to VIP receptors over expressed on breast cancer.

Small molecules (i.e. molecules that are smaller than 1000 Da in size) are proving to be more advantageous as targeting ligands due their affordability, improved stability and small size which allows for easier synthesis and conjugation. The most common small molecule attached to a chemotherapeutic drug for active targeting is folate. Folate binds to surface folate receptors (FR) with very high affinity (KD~1 nm) and is easily internalised through receptor-mediated endocytosis. Other advantages of folic acid as a targeting ligand are that it is stable, non-immunogenic, inexpensive and soluble in organic solvents used for synthesis. Other small molecules used for targeting are carbohydrates such as mannose, glucose and galactose which are recognised by membrane proteins called lectins. An example of this was the targeting to cancer cells of galactosamine conjugated to a doxorubicin bound polymer.

The "chelating agent", also called a chelator, is a bifunctional chelating agent (BFCA) which is a compound consisting of a varied number of heteroatoms, generally O, N or S that are able to complex a radioisotope. The choice of the chelator is determined by the nature and oxidation state of the radioisotope such that the coordination chemistry and donor-ability of the chelator matches the radioisotope properties to form the most stable and inert metal complex.

Chelators used as a BFCA form stable complexes via oxygen, nitrogen and sulphur donor ligands. The stability and pharmacokinetics of the BFCA can also be improved by the modification of the basic alkyl backbone with various functional groups in order to better coordinate the metal.

BFCA's can be classified into two groups: acyclic chelators and cyclic chelators. Acyclic (open chain) chelators generally have faster metal-complexing kinetics than their cyclic counterparts, but are generally more kinetically labile. However, a few acyclic chelators with specific radioisotopes show high thermodynamic stability and kinetic inertness in vitro.

An example of an acyclic chelator is N-diethylenetriaminepentaacetic acid (DTPA) and its analogues. $N_2S_2$ chelators have been used in the labelling of proteins, peptides and oligonucleotides with $^{99m}Tc$ and $^{186}Re$. The simplest of these chelators is N,N'-ethane-bis(aminoethanethiol) (DADT), which is used as the building block for development of further $N_2S_2$ chelators such as N,N'-ethane-bis(1,1-dimethylaminoethanethiol) (BAT-TM), monoamide-monoaminedithiols (MAMA) and N,N'-ethane-bis(mercaptoacetamide) (DADS). The most recent development of $N_2S_2$ chelators is the use of ethylenedicysteine (EC) to chelate $^{99m}Tc$ efficiently and stably (96). $N_3S$ BFCA such as triamidethiols (TAT) are used to complex $^{186}Re$ and $^{188}Re$. Commonly used BFCA in the $N_3S$ series are mercaptoacetyl-glycylglycylglycine (MAG$_3$) and mercaptoacetyl-glycylglycyl-γ-butyric acid (MAG$_2$-GABA). Another acyclic chelator, most specifically for binding Ga(III), is (1,2-bis{[[6-(carboxy)pyridine-2-yl]methyl]-amino}-ethane) (H$_2$dedpa). H$_2$dedpa is a $N_4O_2$ chelator that binds Ga with a stability constant of 28.1.

Bone cancer is an aggressive type of tumour which causes much pain and for which there is no definitive therapy. The only 'treatment' of bone cancer is palliation for the pain experienced as a result of the tumour. Palliative care for patients with bone cancer is accomplished through acyclic chelators radiolabelled with $^{153}Sm$ and $^{117m}Sn$. The first of these chelators comprise nitrogen-containing structures but instead of carboxylic acids as pendant arms, they have phosphonic acid substituents. The FDA-approved radiopharmaceutical for this type is $^{153}Sm$-EDTMP (ethylenediaminetetramethylenephophonic acid) (Quadramet). $^{153}Sm$-EDTMP shows very good pharmacokinetics and in vivo clearance, and was approved for the treatment of painful bone metastases in 1997. The second potential bone therapeutic agent is $^{117m}Sn$-DTPA. $^{117m}Sn$ has two conversion electron emissions of 127 and 129 keV which present shorter penetration ranges and so less bone marrow toxicity.

Cyclic chelating agents form metal complexes that are a lot more stable thermodynamically and kinetically inert. The stereochemistry and coordination of the isotope within the macrocycle together with resultant complex stability is dependent on a number of factors: 1) the size of the ring; 2) the number of substitutions occurring at the N-atoms; 3) the properties of the substituents on the N-atoms; 4) the coordination number of the radioisotope; 5) the metal to ligand ratio used during complexation and the nature of the counter ions used; and 6) the pH of the complexation reaction which will affect the protonation state of the free macrocyclic chelator. Examples of BFCA for radio imaging and therapy are tri- and tetraaza-based amino macrocycles which are then derivatised with carboxyl pendant arms and other moieties for bifunctionality and to increase the stability of the complexes. The most popular of these macrocyclic BFCA are NOTA ((1,4,7-triazacyclononane-1,4,7-triacetic acid), DOTA (1,4,7,10-tetraazacyclododecane-1,4,7,10-tetraacetic acid) and TETA (1,4,8,11-tetraazacyclotetradecane-1,4,8,11-tetraacetic acid), and their analogues.

Analogues of NOTA are NOTASA (1,4,7-triazacyclononane-N-succinic acid-N',N''-diacetic acid) and NODAGA (1,4,7-triazacyclononane-N-glutamic acid-N',N''-diacetic acid, as well as functionalisations of NOTA with a separate conjugation moiety such as a para-isothiocyanato benzyl group (p-NCS-NOTA). NOTA has also been changed to some phosphonate analogues such as NOTP (1,4,7-triazacyclononane-N,N',N''-tris (methylenephosphonic) acid.

The macrocyclicchelators DOTA and TETA are based on the macro cyclescyclen and cyclam respectively. Both these chelators have been used to form stable complexes with a number of different radioisotopes and have been derivatised in various ways to improve metal coordination. The only challenge however with these chelators is that complexation often occurs very slowly and requires elevated temperatures to achieve decent labelled compound yields.

Analogues of DOTA are PA-DOTA (R-[2-(4-aminophenyl)-ethyl]-1,4,7,10-tetraazacyclododecane-1,4,7,10-tetraacetic acid), DOTASA (1,4,7,10-tetraazacyclodecane-1-succinic acid-4,7,10-triacetic acid) and DOTAGA (1,4,7,10-tetraazacyclo-decane-1-glutamic acid-4,7,10-triacetic acid) have altered carboxylate pendant arms. DO3A and DO2A are analogues in which one or two of the carboxylic acid groups have been removed to attach other functionalities to the nitrogen atoms. CB-DO2A includes an ethylene cross bridge between two opposite nitrogens. Derivatives of DOTA in which a substituent is attached to the alkyl backbone include p-NCS-Bz-DOTA (2-(4-isothiocyanatobenzyl)-1,4,7,10-tetraazacyclo-dodecane-N,N',N'',N'''-tetraacetic acid) and the derivatives 1B4M-DOTA (2-methyl-6-(p-isothiocyanato-benzyl)-1,4,7,10-tetraazacyclododecane-1,4,7,10-tetraacetic acid) and CHX-DOTA (2-(p-isothiocyanatobenzyl)-5,6-cyclo-hexano-1,4,7,10-tetraazacyclododecane-1,4,7,10-tetra-acetate) which include an extra substituent onto the p-NCS-Bz-DOTA ring.

TETA is a cyclam macrocyclic ring and similar to DOTA has four nitrogen atoms that each have an acetate group attached to them, however, TETA is a 14-membered ring as opposed to DOTA's 12-membered ring. The extra two carbons in the TETA cyclam ring make for a slightly larger cavity that can offer a slight increase in the stability of some metal coordination. Owing to the high stabilities of radionuclide complexes and the ease at which substitution occurs at the nitrogen atoms, cyclam is one of the macrocycles used most often in the formation of bifunctional chelators. Analogues of TETA are bromoacetamidobenzyl-1,4,8,11-tetraaza-cyclotetradecane-N,N',N'',N'''-tetraacetic acid (BAT), 3-(4-isothiocyanato-benzyl)-1,4,8,11-tetraazacyclotetra-decane-N,N',N'',N'''-tetraacetic acid (p-NCS-Bz-TETA), 4-[(1,4,8,11-tetraazacyclotetra-decane-1-yl)methyl]benzoic acid (CPTA), 4,11-bis(carboxymethyl)-1,4,8,11-tetraazabicyclo [6.6.2]-hexadecane (CB-TE2A), 3,6,10,13,16,19-hexaazabicyclo[6.6.6]icosane (Sar), tetra-(amino methyiphosphonate) cyclam (TEPA).

Below are structures for cyclic chelators.
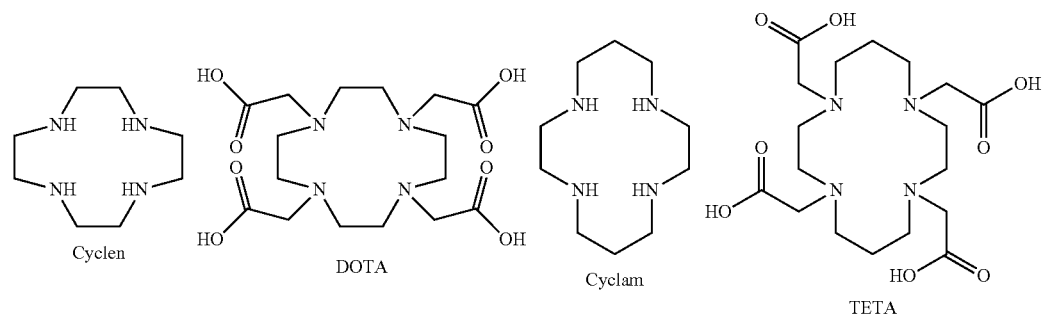
Cyclen · DOTA · Cyclam · TETA
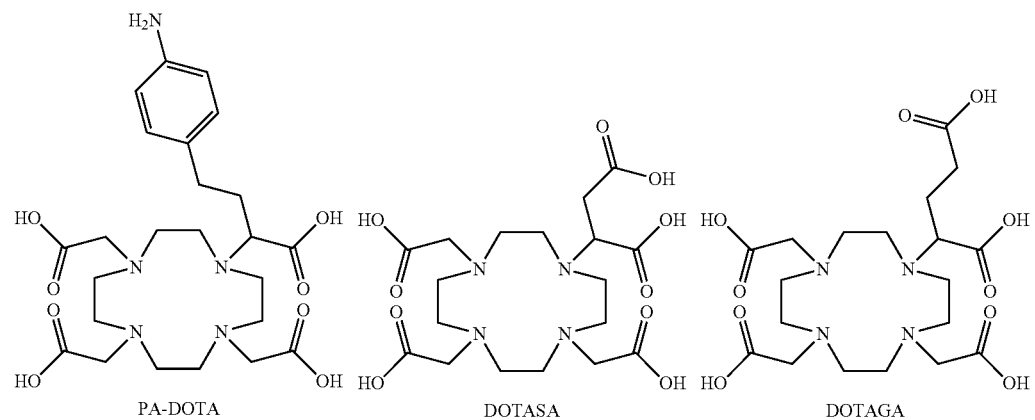
PA-DOTA · DOTASA · DOTAGA
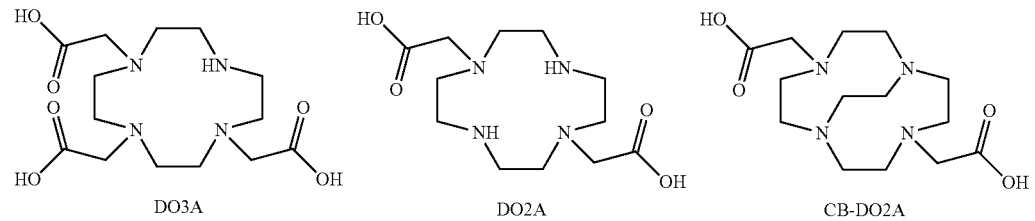
DO3A · DO2A · CB-DO2A
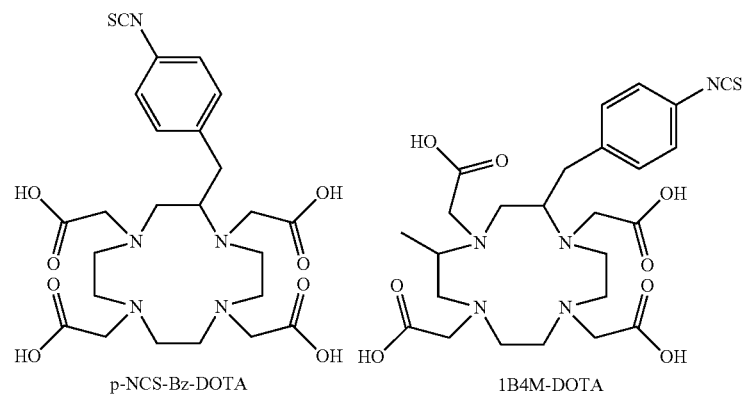
p-NCS-Bz-DOTA · 1B4M-DOTA -continued
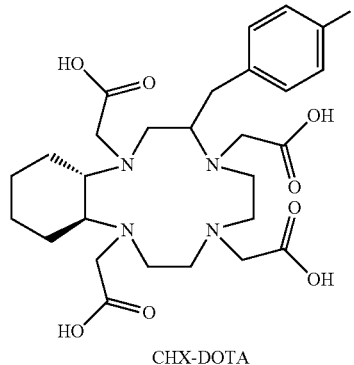
CHX-DOTA
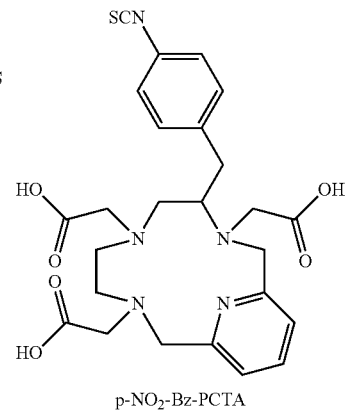
p-NO$_2$-Bz-PCTA
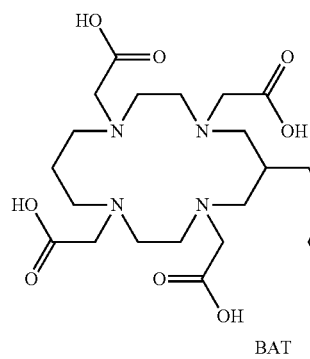
BAT
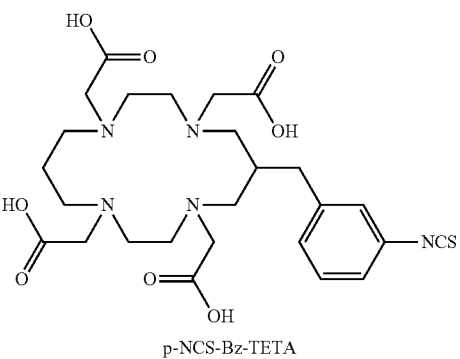
p-NCS-Bz-TETA
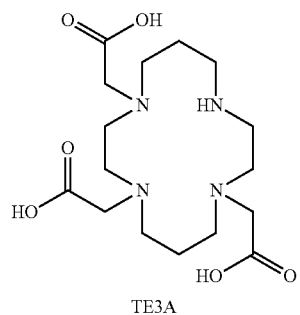
TE3A
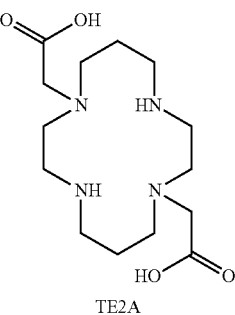
TE2A
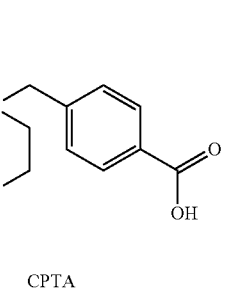
CPTA
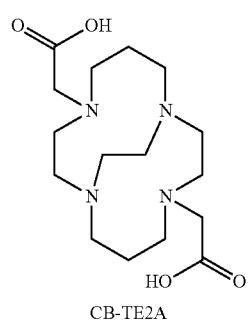
CB-TE2A
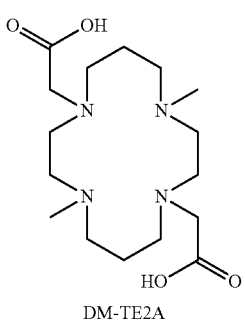
DM-TE2A
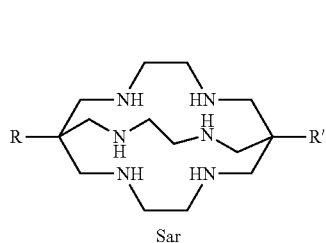
Sar
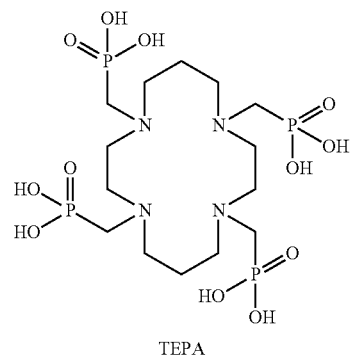
TEPA

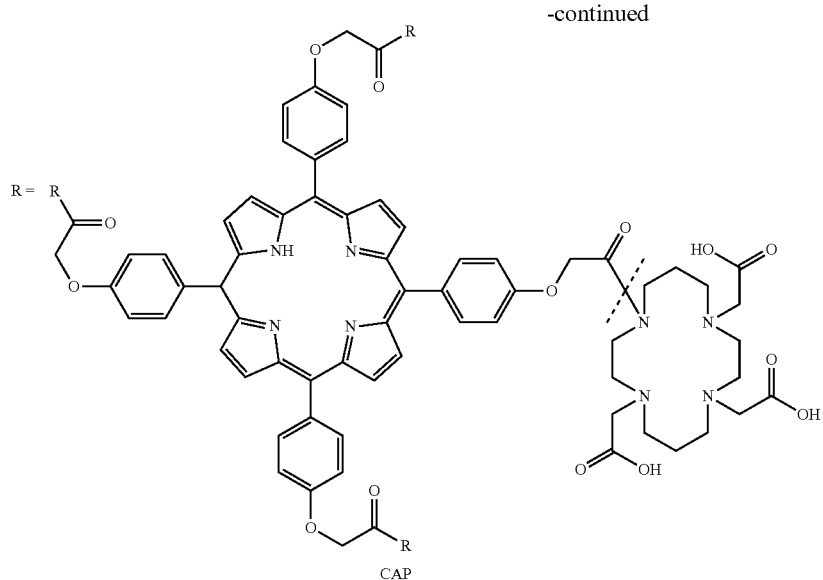

CAP

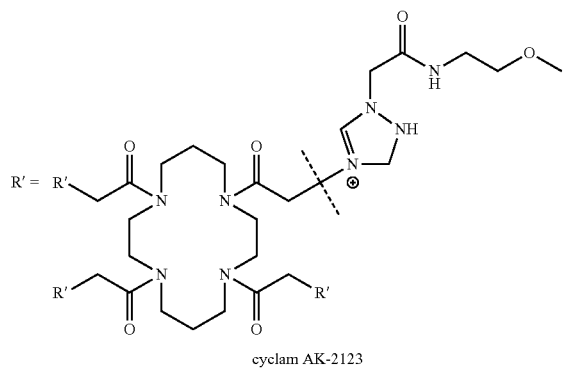

cyclam AK-2123

A "linker" is a carbon chain of a suitable length (4 to 20, typically 8 to 15 carbon atoms) that connects the chelating agent to the EPR agent. The linker within the bioconjugate separates the radionuclide and BFCA from the portion of the radiopharmaceutical that targets the cells through the EPR effect. As such, the linker should not interfere with the ability of the chelate to complex radioisotopes or the affinity and binding of the targeting biomolecule to its specific receptor. The linker can be used to improve the pharmacokinetic properties of the radiopharmaceutical by increasing the lipo or hydrophilicity of the bioconjugate and by containing a metabolisable bond which can be cleaved within the tumour. This allows for internalization of the chelating agent and radionuclide into the cells to deliver the lethal dose of radiation. In the synthesis of the bioconjugate it is also necessary, if possible, to attach the cleavable linker rapidly and at mild temperatures in order to prevent any degradation of thermally sensitive biomolecules.

The properties of the cleavable linkers are such that they can be designed to be degraded within the cell or in very close proximity of the cell. After cleavage the cytotoxic radionuclide chelator is released from the possibly cumbersome biomolecule to allow the radiation source to localise within the cell where it can do the most damage.

Non-cleavable linkers comprise of predominantly four types: peptide, thiourea, thioether and click chemistry triazole bonds. The inherent functionalities of the biomolecules generally include amine or thiol groups which can then be used to couple to an appropriate moiety on the linker and chelator.

Peptide or amide bonds are formed between a carboxylic acid, most often as a pendant arm of a chelator, and a primary amine. Efficient coupling is facilitated by the activation of the carboxylic acid to a better electrophile with the aid of a coupling reagent. These coupling reagents are generally EDC (1-ethyl-3-(3-dimethylaminopropyl)carbodiimide), DCC (dicyclohexylcarbodiimide), HOBt (hydroxyl-benzotriazole) and HATU (O-(7-azabenzotriazol-1-yl)-N, N, NO, NO-tetramethyluronium-hexafluorophosphate), but can also include mixed-anhydride activation methods. One of the amide bond formation techniques most often used is activation of the carboxylic acid with N-hydroxysuccinimide (NHS) to form a succinimidyl ester that can be reacted with amines without any additional coupling reagents. The NHS-activated acids have a high selectivity for aliphatic amines and react optimally at a pH 8-9 in an aqueous environment. Peptide bond formation is a highly favourable coupling technique, but a chelator will often have multiple carboxylic acid groups and the biomolecule multiple amines, and so protection/deprotection strategies or the control of molar ratios is required to limit the amount of couplings that occur onto the biomolecule.

Another type of linker conjugation strategy is the reaction of a primary amine with an isothiocyanate functionality to form a thiourea bond. Isothiocyanates are used to link chelators and targeting agents under slightly basic conditions of pH 8.0-9.5, since a deprotonated amine is required for the nucleophilic addition reaction. Isothiocyanates are more stable in aqueous conditions than the NHS esters, and isothiocyanate aromatic derivatives are often used to couple biomolecules to DTPA and DOTA.

Thioether bonds are formed by the Michael addition of a nucleophilic thiol group to an electrophilic Michael acceptor such as acrylates, acrylamides, vinyl sylfones and maleimides. The high nucleophilicity of the thiol group allows for this thiol-ene coupling to occur under mild physiological conditions without the need for a catalyst or heating. The thioether bond that forms is very stable even under strong basic, acidic or reducing conditions but can react with oxidising agents. A maleimide Michael acceptor is used most often in the formation of radiopharmaceuticals, as acrylates and acrylamides are more reactive and tend to undergo polymerisation. Maleimides react best with thiols at a pH 7.0-7.4. Care needs to be taken with reaction above a pH of 8 as the probability of hydrolysis of the maleimide group to non-reactive maleamic acid increases. The labelling of biomolecules is generally directed at the amino groups of lysine residues, which are abundant within the structure. This increases the chance of labelling but also decreases the control of the labelling percentage. Free thiol groups originate from cysteine residues which are not found in many biomolecules and so it is often required to introduce this functionality by reduction of disulfide bonds. The use of a limited amount of thiol groups for conjugation allows for a greater control of the molar ratios of the compounds reacting thereby obtaining more specific, uniform labelling. Biomolecules that contain thiol groups count amongst a few proteins and antibodies. The most exploited and promising protein in this respect is human serum albumin (HSA) which has a free thiol group at the cysteine-34 position. The thiol groups in antibodies are present as disulfide bonds and so need to be first reduced.

The 'click' reaction is a non-concerted reaction that owes its inspiration to the pericyclic 1,3-dipolar cycloaddition reaction pioneered by Rolf Huisgen in the 1960s. It is so termed for its very fast reaction rate and involves reaction between an alkyne and an azide to form a 1,4-substituted triazole in a regioselective manner. Both alkyne and azide can easily be introduced into either the chelator or the biomolecule leading to the selective and rapid formation of a linked complex in good yields. The challenge with this reaction is the purification to remove the copper catalyst which can become complexed to the chelator, and so a non-copper catalysed click-chemistry reaction has been developed.

Cleavable linkers are most often used in chemotherapeutic drugs but still find application in radiopharmaceuticals. These linkers are designed for the efficient release of the cytotoxic payload within the tumour cells or within close proximity to them. Small hydrophobic drugs can easily cross the plasma membrane of cells through passive diffusion but large macromolecules are not easily able to permeate into the cytosolic space. These large bioconjugates are therefore endocytosed and need to be degraded into smaller components that can cross membrane barriers. The chelator complex is therefore cleaved from the bulky targeting agent to allow for increased localisation of the radioisotope within the cell. Cleavage of linkers is based on a difference in properties between the blood and plasma and internal cellular compartments.

Some types of linkers are cleaved by chemical means and these include acid-labile hydrazone bonds which are sensitive to changes in pH, and disulfide bonds, which are sensitive to glutathione reduction. Hydrazone links are stable within the blood stream and normal interstitial tissue at a pH 7.4-7.6 but will be hydrolysed once the conjugate is internalised into the cell through endocytosis into endosomes (pH 5.0-6.5) and lysosomes (pH 4.5-5.0). The tumour micro-environment surrounding the tumour cells also has a slightly acidic pH of 6.5-6.9, which has been found to cleave the hydrazone bond. Studies have shown that extracellular cleavage will still allow the chelator-radioisotope complex to be taken into the cell but less specifically.

Disulfide bonds are readily reversible and stable covalent linkages formed by the oxidation of two cysteine thiol groups that are found in proteins and antibodies. Disulfides are cleaved by high levels of intracellular glutathione, a thiol containing tri-peptide. Disulfide bonds used in linker strategies are formed by the oxidation of a free thiol group, within a biomolecule, with a sulfhydryl containing BFCA or chemotherapeutic drug. Tumour cells induce a hypoxic, decreased oxygen environment as a result of poor blood flow to the tumour which then leads to an increase in glutathione and reductive enzymes. Glutathione is found at high millimolar intracellular concentration levels but only in micromolar quantities in the blood. The reducing intracellular space thereby results in rapid cleavage of the linker once the compound has been internalised.

Linkers that degrade by chemical means often have limited plasma stability. To improve stability within the blood, linkers that are based on peptides and cleaved by enzymatic means were established. These linkers are susceptible to different enzymes depending on which amino acids are used in the chain. Upregulation of proteases, both intra and extracellular, have been found in many types of cancers and have been seen to play an important role in tumour progression, invasion and metastases. The intracellular cysteine cathepsin enzymes B and S are lysosomal proteases that are associated with protein degradation. These proteases are specific to lysosomes and generally never found in the extracellular environment except in metastatic tumours, and are highly specific for cleaving certain peptide sequences. Cathepsin labile linkers are therefore favourable for radioisotope and drug-delivery strategies, since the bioconjugates are highly stable within the serum but rapidly cleaved within the lysosomes. A number of cleavable peptide sequences for cathepsin B and S have been investigated. Cathepsin B will cleave dipeptide linkers Phe-Lys and Phe-Arg and the more hydrophilic Val-Lys, Val-Citrulline (Cit) and Phe-Cit. Citrulline is isoteric and isoelectric to Arg but not as basic. Some tetrapeptide linkers that have been used for cleavage by cathepsin B are Gly-Gly-Gly-Phe, Gly-Phe-Leu-Gly and Ala-Leu-Ala-Leu. Cathepsin S cleaves the sequence Pro-Met-Gly-Leu-Pro. A number of other proteases are also found within the cell and its environment and peptide linkers have been developed that target these enzymes for cleavage. Thermolysin is used to cleave an Ala-Val dipeptide while prolineendopeptidase releases cytotoxic moieties linked with Ala-Pro or Gly-Pro. These linkers have connected drugs such as doxorubicin and radioisotopic chelators such as $^{177}$Lu-DOTA and $^{90}$Y-DOTA to the polymers HMPA and PEG and monoclonal antibodies for cancer therapy.

Matrix metalloproteases (MMP) are endopeptidases that are important for the degradation of the extracellular matrix and basement membranes. Within tumour cells, the increase of MMP's plays a critical role in tumour progression and cell invasion leading to tumour metastases. MMP can cleave peptide sequences, and an octapeptide linker was developed, Gly-Pro-Leu-Gly-Ile-Ala-Gly-Gln, which is targeted by over expressed MMP-2 and MMP-9 in certain cancer types. This peptide was used to link doxorubicin to an albumin macromolecule for release and accumulation of the drug within the tumour cells.

Radiopharmaceuticals are multi-component and so in designing a therapeutic radiopharmaceutical, all of the properties must be assessed. The radionuclide should have a favourable half-life and decay properties for therapeutic purposes, and if possible, be easy to obtain and affordable. The chelator should match the radioisotope in terms of half-life and form a thermodynamically stable and kinetically inert complex with the chosen radionuclide. The radionuclide should be bound sufficiently tightly to the chelator such that no transchelation of the metal occurs with any metal-binding plasma proteins. Ideally, the radiolabelling of the chelator should occur under low concentrations in minimal time and at minimal temperatures to preserve any biological molecules present. The targeting agent used in the radiopharmaceutical is attached to the chelator through a linker and the agents' affinity for its specific receptor should not be influenced by the chelator. The targeting agent should ideally only accumulate the radiopharmaceutical at the tumour site, and any other free radiobioconjugate should be rapidly excreted from the system to reduce damage to healthy cells.

The nuclide properties to consider include the gamma and particulate emission and half-life. Particulate emission consists of α- or β-emissions (in the range of approx. 100-10,000 keV) and Auger electron emissions (1-100 keV). α- and β-emitters have greater tissue penetration which also damages surrounding healthy tissue whereas Auger electrons have a penetration range of only up to 500 nm which can minimise healthy tissue damage if the nuclide can be delivered to the tumor cells. The complication with the Auger electrons is that they need to be delivered in close proximity to the DNA to have maximum effectiveness. The ideal half-life for a therapeutic agent would be 1-14 days. Current applications for radiotherapy include treatment of large tumors with $^{47}$Sc, $^{90}$Y, $^{131}$I, $^{177}$Lu, $^{188}$Re; micrometastases with $^{117m}$Sn and other short range Auger emitters; leukemia and lymphomas with $^{47}$Sc, $^{117m}$Sn, $^{67}$Cu and $^{131}$I; and treatment on some neuroendocrine tumors with $^{111}$In. Bone metastases occur in a large percentage of prostate cancer sufferers and result in a significant increase in morbidity due to severe pain and treatment is only palliative. The nuclides used for this treatment are $^{89}$Sr, $^{153}$Sm, $^{117m}$Sn, $^{32}$P and $^{186}$Re. Besides radiotherapy, a lot of these radionuclides are also applied in the radio imaging of tumors.

Examples of radionuclides that may be used for imaging (diagnosis) include $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, $^{123}$I.

Examples of radionuclides that may be used for therapeutic purposes include:

$^{188}$Re, $^{186}$Re, $^{153}$Sm, $^{166}$Ho, $^{90}$Y, $^{89}$Sr, $^{111}$In, $^{153}$Gd, $^{67}$Cu, $^{64}$Cu, $^{198}$Au, $^{199}$Au, $^{177}$Lu, $^{32}$P, $^{161}$Tb and $^{33}$P are preferred (beta) β-emitters which may also emit γ (gamma) radiation;

$^{225}$Ac, $^{212}$Bi, $^{213}$Bi, $^{211}$At, $^{223}$Ra, $^{224}$Ra, $^{227}$Th are preferred α(alpha)-emitters which also may emit γ (gamma) radiation.

$^{58m}$Co, $^{61}$Cu, $^{103}$Pd, $^{103m}$Rh, $^{111}$In, $^{117m}$Sn, $^{119}$Sb, $^{161}$Ho, $^{193m}$Pt, $^{195m}$Pt, $^{197}$Pt, $^{201}$Tl, $^{203}$Pb, $^{161}$Tb are preferred Auger/conversion electron emitters which also may emit γ (gamma) radiation;

Preferred radionuclides are Auger electron emitting radionuclides. These are radionuclides that emit Auger electrons which are very low energy (<500 eV) electrons with a very short, nanometer range that are emitted from the outer shell of a decaying atom during the rearrangement of the electron shells due to electron capture or internal electron conversion processes. Such radionuclides include $^{111}$In, $^{203}$Pb, $^{201}$Ti, $^{103}$Pd, $^{103m}$Rh, $^{119}$Sb, $^{58m}$Co, $^{161}$Ho, $^{161}$Tb, $^{61}$Cu, $^{67}$Cu, $^{195m}$Pt, $^{193m}$Pt, $^{117m}$Sn.

Further aspects of the invention include modification of the EPR agent for attachment to the linker and modification of the metabolite for attachment to the chelator and/or the linker; as well as modification of the linker and chelator.

A radiopharmaceutical bioconjugate in accordance with an embodiment of the invention is produced by joining three synthetic components:

1) a metabolite that targets tumour cells, preferably a glucose containing linker that is functionalised for connection to the chelating agent through alkylation or acylation
2) a chelating agent, preferably a cyclam functionalised through N-linkages for radioisotope chelation; and
3) a cleavable linker, preferably a linker functionalised with maleimide for attachment to EPR agent to form a pro-conjugate before linking to:
4) biomolecule/EPR agent, preferably albumin.

Albumin has a size of 66.5 kDa, is very soluble, stable, readily available and biodegradable as well as lacking toxicity and immunogenicity.

The metabolite that targets tumour cells target is glucose. Tumor cells have a very high turnover and growth and as such require a large amount of glucose which is taken up through over-expressed glucose transporters on the cell surface.

The chelating agent is a TETA derivative which will allow chelation to a number of radionuclides and can be modified to link the glucose target and the albumin carrier.

The radionuclide is $^{103}$Pd due to its 17 day half-life and favourable, short range, 21 keV x-ray and Auger electron emissions as it decays through $^{103m}$Rh to $^{103}$Rh. Other nuclides can however be used for imaging of the macromolecule in vivo, to test for localisation and biodistribution of the compound.

The attachment of the EPR agent may take place in vitro or in vivo, to produce the radiopharmaceutical bioconjugate. The bioconjugate is illustrated below:

The synthesis of the pro-conjugate (glucose-cyclam-cleavable linker without the albumin EPR agent) requires the careful manipulation of a variety of different functional groups to connect all the required components:

the functionalization of the glucose metabolite requires that suitable protection strategies for the hydroxyl groups be carried out. The glucose metabolite is then reacted with the terminal hydroxyl group of a suitable length chain with a terminal bromide or hydroxyl group to form a glucose metabolite connected to a carbon chain with a terminal bromide group or a hydroxyl group that can be oxidized to an acid chloride;

the functionalization of the linker requires that an alkyl chain of suitable length with suitable functional groups for substitution be converted into a linker by the connection of two suitable fragments: the first fragment with an alkyl halide at one end for attachment to the chelating agent and the second fragment with a protected amine at the other end.

the functionalization of the cyclam chelator requires that the cyclam is first mono-alkylated with the linker through an $S_N2$ reaction and then alkylated a second time with the metabolite though an $S_N2$ or $S_NAc$ reaction. The remaining amines of the macrocycle are then reacted with tertiary-butyl bromoacetate groups that will assist in metal complexation. A deprotection strategy of all hydroxyl, carboxylic acid and amine protected functional groups is then carried out. The terminal amine is then converted into a maleimide to bind to the EPR agent.

Radiolabelling is carried out by dissolving the pro-conjugate in water. To the pro-conjugate is added an aqueous solution of the radioisotope to effect radiolabeling.

Formulations containing the bioconjugates and proconjugates described above may comprise these bioconjugates or proconjugates that have already been radiolabelled or not, in an aqueous solution. If a specific pro-conjugate is not water soluble then small amounts of ethanol or dimethylsulfoxide can be used at such levels that are not toxic to the cells. Complexation to a radioisotope may be done in kit form which includes a sealed container with a predetermined amount of pro- or bioconjugate as well as a reducing agent if necessary for labeling to which is added the radioisotope in an aqueous solution. The kits may also contain pharmaceutical adjunct material such as pharmaceutical grade salts for osmotic pressure, buffers, preservatives, anti-oxidants and such. The components of the kit may be in liquid, frozen or dry form.

Proconjugates and bioconjugates of the present invention may be used in the diagnosis and treatment (including palliative care) of cancer; primary or secondary, benign or malignant tumors. The selective uptake in tumor areas and cells will allow targeted delivery of radionuclides that will minimize radiation to other sensitive surrounding tissue such as bone marrow. The present invention will work better in fast growing solid tumours such as osteosarcoma while for metastatic cancer the primary aim would be (secondary) bone metastasis. The following general cancers have also been shown to have a much higher percentage of the glucose transporter, GLUT1, and may also be targeted by the radiopharmaceutical conjugates exemplified:

Colorectal cancer
Renal cell carcinoma
Breast cancer
Stomach cancer
Head and Neck carcinoma
Sarcomas.

Methods of diagnosis and therapeutic treatment require the administration of the radiolabelled conjugates as an intravenous or intraperitoneal dose in sterile saline or plasma. The unit dose to be administered has a radioactivity of about 0.01-300 mCi and the solution injected with this dose is 0.1-10 mL.

Companion diagnostics is the term used where the diagnostic equivalent (molecule radiolabelled with a diagnostic radionuclide) of the therapeutic agent is used prior to therapy to individualise the dose the specific patient will receive of the therapeutic agent. This enables the individualisation of patient doses. The therapeutic agent can be the molecule not being radiolabelled as well as the molecule radiolabelled with a therapeutic radionuclide. The latter is also referred to as Teranostic (or Theranostic) agents where pairing of radionuclide is used to achieve both diagnosis and therapy with the same agent/molecule. It may be administered in two separate doses (preferred) or in a single administration. Some of the listed radionuclides may be used as diagnostic and therapeutic radionuclide or both in the same or separate administrations.

EXAMPLES

Example 1

Radiolabelled Metabolite-Chelator-Linker Pro-Conjugate for Attachment to an EPR Agent and Formation of a Radiopharmaceutical Bioconjugate A) Two proposed synthetic glucose-cyclam-maleimide pro-conjugates with various linker alternatives that are radiolabelled with $^{103}$Pd. B) Michael addition of the free thiol in albumin to the maleimide of the pro-conjugates to form the radiopharmaceutical bioconjugate.

Example 2

Metabolite—Synthesis of Glucose Linker
10-(tert-butyldiphenylsilyloxy)decan-1-ol (1)

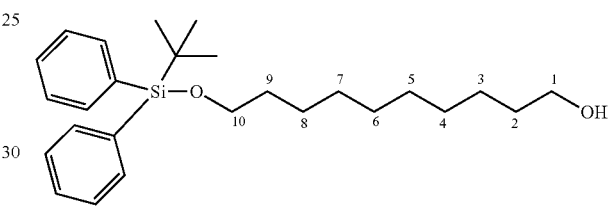

Imidazole (3.50 g, 51.7 mmol), followed by TBDPSCI (8.70 g, 31.5 mmol) was added slowly to a solution of 1,10-decanediol (5.00 g, 28.7 mmol) in dry THF (60 mL) under $N_{2(g)}$ and left stirring at room temperature for 24 hrs. The reaction was quenched by evaporation of THF in vacuo followed by addition of water (60 mL) and $CH_2Cl_2$ (60 mL). The organic phase was separated and extracted with water (2×50 mL) and washed with brine (50 mL). The organic phase was dried, filtered and concentrated. The crude product was columned [Hexane:EtOAc (9:1)] and pure alcohol obtained as an oil (6.59 g, 56%). $R_f$=0.42 (Hexane:EtOAc 8:2).

2,3,4,6-Tetra-O-benzoyl-α-D-glucopyranosyl Benzoate (2)

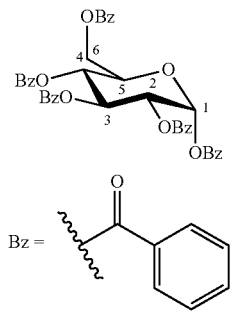

Benzoyl chloride (4.68 g, 33.3 mmol) was added dropwise to a solution of α-D-glucose (1.0 g, 5.6 mmol) in pyridine (30 mL) at 0° C. After 10 min at 0° C., the solution was stirred for 2 hrs at room temperature. The reaction was quenched by addition of cold water (50 mL) and the product extracted with EtOAc (3×50 ml). The combined organic layers were washed with 1N HCl (3×50 mL) followed by brine (50 mL) and then dried, filtered and concentrated. The crude product was purified by recrystallisation with hot Hexane:EtOAc 2:1 to give the title compound as a white solid (3.48 g, 89%). $R_f$=0.28 (Hex:EtOAc 8:2).

$\delta_H$ (CDCl$_3$, 400 MHz): 8.16 (2H, d, J=8.0 Hz, H—Ar), 8.02 (2H, d, J=8.0 Hz, H—Ar), 7.94 (2H, d, J=8.0 Hz, H—Ar), 7.88 (4H, d, J=8.0 Hz, H—Ar), 7.66 (1H, t, J=8.0 Hz, H—Ar), 7.53-7.28 (14H, m, H—Ar), 6.85 (1H, d, J=4.0 Hz, H-1), 6.32 (1H, t, J=8.0 Hz, H-3), 5.85 (1H, t, J=8.0 Hz, H-4), 5.68 (1H, dd, J=4.0, 8.0 Hz, H-2), 4.62 (2H, m, H-6a/H-5), 4.59 (1H, dd, J=4.0 Hz, J=12.0 Hz, H-6b)

$\delta_C$ (CDCl$_3$, 100 MHz): 166.1, 165.9, 165.3, 165.1, 164.4 (C=O), [133.9, 133.5, 133.4, 133.3, 133.1 130.0, 129.9 (×2), 129.8 (×2), 129.6, 129.0, 128.9, 128.8, 128.6, 128.4 (×3), 128.37 ArC)], 90.0 (C-1), 76.6 (C-3), 70.5 (C-2), 70.5 (C-5), 68.9 (C-4), 62.5 (C-6)

1-Iodo-2,3,4,6-Tetra-O-benzoyl-α-D-glucopyranoside (3)

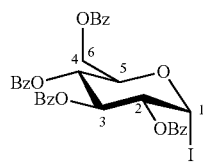

Hexamethyldisilane (0.531 g, 3.63 mmol) in CH$_2$Cl$_2$ (10 mL) was added to a solution of α-D-glucose-pentabenzoate (2) (4.10 g, 5.85 mmol) in CH$_2$Cl$_2$ (60 mL). To this solution was added ZnI$_2$ (0.467 g, 1.46 mmol), followed by I$_2$ (0.921 g, 3.63 mmol) and stirred for 16 hrs. The reaction was quenched by addition of CH$_2$Cl$_2$ (40 mL) and an aqueous solution (120 mL) of NaHCO$_3$ (1.68 g) and Na$_2$S$_2$O$_3$ (1.12 g) and then stirring for 10 min until the pinkish colour and milky solution had cleared. The organic phase was separated and washed with brine (50 mL) and the combined aqueous phases extracted with CH$_2$Cl$_2$ (2×50 mL). The combined organic extracts were dried over MgSO$_4$, filtered and concentrated in vacuo to yield a crude oil of the title compound which was used directly in the next reaction.

10-bromodecyl-tetra-O-benzoyl-β-D-glucopyranoside (4)

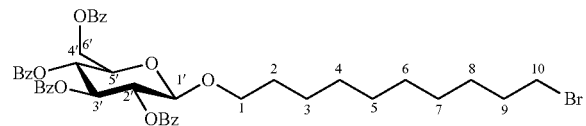

Previously prepared iodide 3 (1.81 g, 2.57 mmol) was dissolved in CH$_2$Cl$_2$ (40 mL) under N$_{2(g)}$ and 4 Å Molecular Sieves (4.00 g) along with ZnCl$_2$ (0.525 g, 3.85 mmol), and 10-bromodecanol (0.914 g, 3.85 mmol) in CH$_2$Cl$_2$ (5 mL) were added to the solution. The reaction was stirred for 17 hrs after which the colour of the solution had changed to a light pink. EtOAc (60 mL) was added and the reaction was quenched by addition of an aqueous solution (80 mL) of NaHCO$_{3(s)}$ (1.80 g) and Na$_2$S$_2$O$_{5(s)}$ (2.40 g). The colour changed from a yellow-orange to a milky white after stirring for 10 min. The solution was filtered through a Celite pad and the phases separated. The organic phase was washed with brine and the combined aqueous phases extracted with EtOAc (2×30 mL). The combined organic layers were dried, filtered and concentrated to yield a crude oil (2.99 g), which was purified by column chromatography (Hexane:EtOAc 8:2). The title product was obtained as a clear oil (1.23 g, 59% over 2 steps). $R_f$=0.48 (Hex:EtOAc 8:2).

$\delta_H$ (CDCl$_3$, 400 MHz): 8.0-7.80 (8H, m, ArH), 7.53-7.24 (12H, m, ArH), 5.89 (1H, t, J=9.6 Hz, H-3'), 5.65 (1H, t, J=9.6 Hz, H-4'), 5.49 (1H, dd, J=7.8, 9.7 Hz, H-2'), 4.81 (1H, d, J=7.8 Hz, H-1'), 4.61 (1H, dd, J=3.3, 12.0 Hz, H-6a'), 4.49 (1H, dd, J=5.2, 12.0 Hz, H-6b'), 4.13 (1H, m, H-5'), 3.89 (1H, dt, J=6.3, 9.6 Hz, H-1a), 3.52 (1H, dt, J=6.7, 9.6 Hz, H-1b), 3.37 (2H, t, J=6.6 Hz, H-10), 1.80 (2H, qn, J=9.6 Hz, H-9), 1.55-1.45 (2H, m, H-2), 1.41-1.30 (2H, m, Alk-H), 1.19-1.05 (10H, m, Alk-H).

$\delta_C$ (CDCl$_3$, 100 MHz): [166.2, 165.8, 165.2, 165.1 (C=O)], [133.4, 133.2, 133.1, 133.0, 129.8 (×2), 129.7 (×2), 129.6, 129.5, 128.9, 128.8, 128.4, 128.3, 128.3, 128.2 (ArC)], 101.3 (C-1'), 73.0 (C-3'), 72.2 (C-5'), 72.0 (C-2'), 70.3 (C-1), 69.9 (C-4'), 63.3 (C-6'), 33.9 (C-10), 32.8, 29.4, 29.3, 29.2, 29.1, 28.7, 28.1, 25.7 (C-Alk).

10-(tert-butyldiphenylsilyloxy)decyl-tetra-O-benzoyl-β-D-glucopyranoside (5)

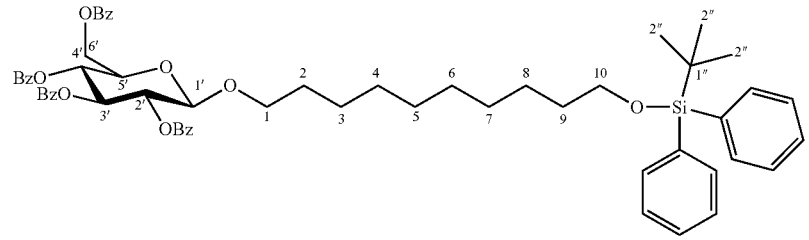

Molecular sieves (7.00 g), ZnCl$_2$ (1.43 g, 10.5 mmol) and alcohol 1 (2.17 g, 5.25 mmol) in CH$_2$Cl$_2$ (15 mL) was added to freshly prepared iodide 3 (3.71 g, 5.25 mmol) in CH$_2$Cl$_2$ (60 mL) and the reaction stirred for 8 hrs. CH$_2$Cl$_2$ (40 mL) was added to the solution and the molecular sieves were filtered off through a celite pad followed by the addition of an aqueous solution (100 mL) of NaHCO$_3$ (0.960 g) and Na$_2$S$_2$O$_3$ (1.44 g) and stirred for 10 min. The organic layer was separated and the aq. phase extracted with CH$_2$Cl$_2$ (3×50 mL). The combined organic layers were washed with brine and aq. phase extracted once more with CH$_2$Cl$_2$ (50 mL). The organic extracts were dried over MgSO$_4$, filtered and concentrated in vacuo to yield a crude oil product which was dry-loaded onto a prepacked column and purified using column chromatography (Hex:EtOAc 9:1, 8:2, 7:3) to yield the title compound as an oil product (3.55 g, 68%). $R_f$=0.51 (Hex:EtOAc 8:2)

$\delta_H$ (CDCl$_3$, 400 MHz): 8.05-7.83 (8H, m, ArH), 7.68 (4H, m, ArH), 7.55-7.26 (18H, m, ArH), 5.91 (1H, t, J=9.6 Hz, H-3'), 5.68 (1H, t, J=9.6 Hz, H-4'), 5.53 (1H, dd, J=7.8, 9.6 Hz, H-2'), 4.85 (1H, d, J=7.8 Hz, H-1'), 4.65 (1H, dd, J=3.3, 12.0 Hz, H-6a'), 4.52 (1H, dd, J=5.2, 12.0 Hz, H-6b'), 4.17 (1H, m, H-5'), 3.92 (1H, dt, J=6.3, 9.6 Hz, H-1a), 3.66 (2H, t, J=6.6 Hz, H-10), 3.55 (1H, dt, J=6.7, 9.6 Hz, H-1b), 1.59-1.50 (4H, m, H-2/9), 1.29 (2H, m, H-8), 1.22-1.00 (10H, m, AlkCH$_2$), 1.04 (9H, s, H-2").

$\delta_C$ (CDCl$_3$, 100 MHz): [166.1, 165.8, 165.2, 165.0 (C=O)], [135.6 (×4), 134.2 (×2), 133.4, 133.2, 133.1, 133.0, 129.8 (×2), 129.7 (×6), 129.5 (×2), 128.9 (×2), 128.4 (×2), 128.3 (×4), 128.3 (×2), 128.3 (×2), 127.5 (×4) (ArC)], 101.3 (C-1'), 73.0 (C-3'), 72.2 (C-2'), 72.0 (C-5'), 70.3 (C-1), 70.0 (C-4'), 64.0 (C-10), 63.3 (C-6'), 32.6, 29.5, 29.4, 29.4, 29.3, 29.2, 26.9 (C-2"), 25.8, 25.7, 19.2 (C-1").

10-hydroxydecyl-tetra-O-benzoyl-β-D-glucopyranoside (6)

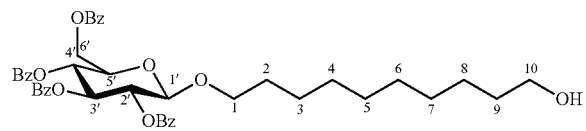

Acetic acid (0.245 g, 4.09 mmol) and N-tetra butyl ammonium fluoride (6.80 mL, 1.0M in THF, 6.80 mmol) was added to a solution of TBDPSO-C10-glucopyranoside 5 (3.38 g, 3.40 mmol) in THF (100 mL) and stirred for 36 hrs. The solvent was evaporated to yield a residue to which H$_2$O (50 mL) was added and then extracted with EtOAc (3×50 mL). The combined organic extracts were washed with brine (50 mL), dried over MgSO$_4$, filtered and concentrated. The crude material was purified with column chromatography (Hex:EtOAc 2:1) to yield the title alcohol as a clear oil (2.30 g, 90%) R$_f$=0.16 (Hex:EtOAc 2:1), $\delta_H$ (CDCl$_3$, 300 MHz): 8.02-7.81 (8H, m, ArH), 7.56-7.25 (12H, m, ArH), 5.90 (1H, t, J=9.6 Hz, H-3'), 5.67 (1H, t, J=9.6 Hz, H-4'), 5.51 (1H, dd, J=7.8, 9.6 Hz, H-2'), 4.83 (1H, d, J=7.8 Hz, H-1'), 4.63 (1H, dd, J=3.3, 12.0 Hz, H-6a'), 4.51 (1H, dd, J=5.2, 12.0 Hz, H-6b'), 4.18-4.12 (1H, m, H-5'), 3.90 (1H, dt, J=6.3, 9.6 Hz, H-1a), 3.62 (2H, t, J=6.6 Hz, H-10), 3.53 (1H, dt, J=6.7, 9.6 Hz, H-1b), 1.63-1.46 (4H, m, AlkCH$_2$), 1.35-1.05 (12H, m, AlkCH$_2$).

$\delta_C$ (CDCl$_3$, 100 MHz): [166.1, 165.8, 165.2, 165.1 (C=O)], [133.4, 133.2, 133.1, 133.0, 129.8, 129.7, 129.6, 129.4, 128.9, 128.4, 128.3, 128.2 (ArC)], 101.3 (C-1'), 73.0 (C-3'), 72.2 (C-2'), 72.0 (C-5'), 70.3 (C-1), 69.9 (C-4'), 63.3 (C-6'), 63.1 (C-10), 32.8, 29.4, 29.4, 29.3, 29.3, 29.1, 25.7, 25.6.

10-(tetra-O-benzoyl-β-D-glucopyranos-1-yl)-decanal (7)

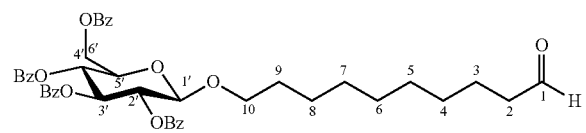

Dess-Martin periodinane (0.59 g, 1.4 mmol) was added to a solution of alcohol 6 (0.870 g, 1.16 mmol) in anh. CH$_2$Cl$_2$ (60 mL) and stirred for 1.5 hrs. The reaction was quenched by the addition of sat. aq. NaHCO$_3$ solution (60 mL) and stirred for 15 min. The aqueous phase was extracted with CH$_2$Cl$_2$ (3×50 mL). The combined organic phase was washed with brine (50 mL), dried over MgSO$_4$, filtered and concentrated. The crude material was purified with column chromatography (Hex:EtOAc 6:4) to yield the title compound as a clear oil (0.693 g, 79%), R$_f$=0.75 (Hex:EtOAc 1:1).

$\delta_H$ (CDCl$_3$, 300 MHz): 9.75 (1H, t, J=1.5 Hz, H-1), 8.02-7.82 (8H, m, ArH), 7.56-7.23 (12H, m, ArH), 5.90 (1H, t, J=7.2 Hz, H-3'), 5.67 (1H, t, J=7.2 Hz, H-4'), 5.51 (1H, dd, J=7.5, 6.0 Hz, H-2'), 4.83 (1H, d, J=6.0 Hz, H-1'), 4.63 (1H, dd, J=2.4, 9.0 Hz, H-6a'), 4.51 (1H, dd, J=4.2, 9.0 Hz, H-6b'), 4.14 (1H, m, H-5'), 3.91 (1H, dt, J=4.8, 7.2 Hz, H-10a), 3.54 (1H, dt, J=4.8, 7.2 Hz, H-10b), 2.38 (2H, dt, J=1.2, 5.4 Hz, H-2), 1.60-1.47 (4H, m, AlkCH$_2$), 1.27-1.05 (10H, m, AlkCH$_2$).

$\delta_C$ (CDCl$_3$, 100 MHz): 202.7 (C-1), [166.1, 165.8, 165.2, 165.0 (C=O)], [133.3, 133.1, 133.1, 133.0, 129.8 (×2), 129.7 (×2), 129.4, 128.9, 128.4 (×2), 128.3 (×2), 128.2 (×2)(ArC)], 101.3 (C-1'), 73.0 (C-3'), 72.2 (C-2'), 72.0 (C-5'), 70.2 (C-10), 69.9 (C-4'), 63.3 (C-6'), 43.8 (C-2), 29.3, 29.1, 29.1, 29.1, 29.0, 25.7, 22.0 (C-Alk).

10-(tetra-O-benzoyl-β-D-glucopyranos-1-yl)decanoic acid (8)

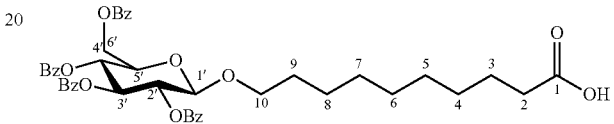

An aqueous solution (4.0 mL) of NaClO$_2$ (0.157 g, 1.7 mmol) and NaH$_2$PO$_4$ (0.208 g, 1.30 mmol) was added to a solution of aldehyde 7 (1.00 g, 1.30 mmol) and 2-methyl-2-butene (0.626 g, 8.90 mmol) in t-butanol (40 mL) and the solution stirred for 2.5 hrs until all the yellow colour had disappeared. The solvent was evaporated to yield a crude oil which was redissolved in CH$_2$Cl$_2$ (50 mL) and H$_2$O (100 mL). The solution was acidified with 1M HCl (10 mL) and the aqueous phase extracted with CH$_2$Cl$_2$ (3×50 mL). The combined organic extracts were dried over MgSO$_4$, filtered and concentrated. The crude material was purified with column chromatography (Hex:EtOAc 1:1) to yield the title compound as a clear oil (0.90 g, 89%) R$_f$=0.39 (Hex:EtOAc 1:1)

$\delta_H$ (CDCl$_3$, 300 MHz): 8.03-7.81 (8H, m, ArH), 7.53-7.26 (12H, m, ArH), 5.91 (1H, t, J=9.6 Hz, H-3'), 5.67 (1H, t, J=9.6 Hz, H-4'), 5.52 (1H, dd, J=7.8, 9.6 Hz, H-2'), 4.83 (1H, d, J=7.8 Hz, H-1'), 4.64 (1H, dd, J=3.4, 12.1 Hz, H-6a'), 4.51 (1H, dd, J=5.2, 12.1 Hz, H-6b'), 4.19-4.13 (1H, m, H-5'), 3.91 (1H, dt, J=6.2, 9.7 Hz, H-10a), 3.54 (1H, dt, J=6.2, 9.7 Hz, H-10b), 2.32 (2H, t, J=7.4 Hz, H-2), 1.62-1.46 (4H, m, AlkCH$_2$), 1.27-1.02 (10H, m, AlkCH$_2$).

$\delta_C$ (CDCl$_3$, 100 MHz): 179.1 (C=O), [166.1, 165.8, 165.2, 165.0 (C=O)], [133.4, 133.2, 133.0, 129.8, 129.7, 129.6, 129.4, 128.9, 128.4, 128.3, 128.2 (ArC)], 101.3 (C-1'), 73.0 (C-3'), 72.2 (C-2'), 72.0 (C-5'), 70.3 (C-10), 69.9 (C-4'), 63.3 (C-6'), 33.9 (C-2), 29.3, 29.1, 29.1, 29.0, 28.9, 25.7, 24.6 (C-Alk)

10-(tetra-O-benzoyl-β-D-glucopyranos-1yl)decanoyl chloride (9)

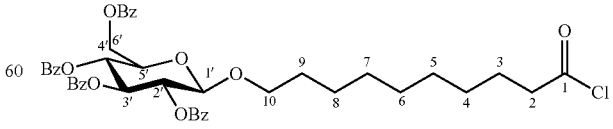

A few drops of DMF were added to a solution of decanoic acid 8 (0.900 g, 1.17 mmol) in anh. CH$_2$Cl$_2$ (30 mL) under N$_{2(g)}$. The flask was placed at 0° C. and oxalyl chloride (0.11 mL, 1.29 mmol) was added dropwise to the solution. The reaction was left stirring for 1 hr after which the solvent was removed under vacuum. A small amount of toluene (5 mL) was added and again evaporated in vacuo and the residue was then dried under a vacuum pump for 10 min to remove any remaining oxalyl-Cl. The crude oil product was not characterised but used directly in the next acylation reaction.

Example 3

Linker—Synthesis of Non-Cleavable Linker
10-Hydroxydecyl-phthalimide (10)

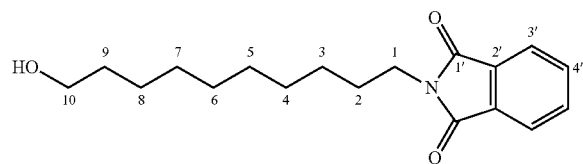 [SMILES: O=C1c2ccccc2C(=O)N1CCCCCCCCCCO]

Potassium phthalimide (3.50 g, 18.9 mmol) was added to a solution of 10-bromodecanol (4.48 g, 18.9 mmol) in DMF (50 mL). The mixture was heated at 100° C. for 20 hrs after which most of the DMF was distilled off. The remaining product was redissolved in $CH_2Cl_2$ and then washed with $H_2O$ (2×50 mL). The combined organic layer was dried over $MgSO_4$, filtered and concentrated in vacuo to yield a crude solid which was purified using column chromatography (Hex:EtOAc 6:4). The title compound was obtained as a white solid (4.92 g, 97%). $R_f$=0.45 (Hex:EtOAc 1:1). $\delta_H$ ($CDCl_3$, 300 MHz): 7.84-7.81 (2H, m, ArH), 7.70-7.68 (2H, m, ArH), 3.66 (2H, t, J=7.2 Hz, H-1), 3.62 (2H, t, J=6.8 Hz, H-10), 1.66 (2H, qn, J=8.0 Hz, H-2), 1.55 (2H, qn, J=8.0 Hz, H-9), 1.42 (1H, s, —OH), 1.32-1.25 (12H, m, Alk-$CH_2$)

$\delta_C$ ($CDCl_3$, 100 MHz): 168.4 (C=O), 133.8 (Ar-3'), 132.2 (ArC-2'), 123.1 (ArC-4'), 63.0 (C-10), 38.0 (C-1), 32.8 (C-9), [29.4, 29.3, 29.3, 29.0, 28.5, 26.8, 25.6 (Alk-$CH_2$)]

10-aminodecan-1-ol (11)

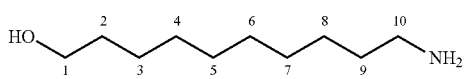

Hydrazine hydrate (0.81 g, 0.78 mL, 25.3 mmol) was added to a solution of 10-hydroxydecyl-phthalimide (10) (4.50 g, 14.8 mmol) in EtOH (180 mL) and refluxed overnight. Starting material remained and so extra hydrazine (0.4 ml) was added and the solution again refluxed overnight. The solvent was evaporated and the crude solid product redissolved in $CH_2Cl_2$ (100 mL) and basified with 2M NaOH until all solid had dissolved. The organic layer was separated out and the aqueous phase extracted with $CH_2Cl_2$ (2×80 mL). The combined organic layer was dried over $MgSO_4$, filtered and concentrated in vacuo. The crude white solid obtained was recrystallised ($CH_2Cl_2$:Hexane) to yield the title compound as a white solid (2.22 g, 88%). $R_f$=0.07 ($CH_2Cl_2$:MeOH 9:1 $\delta_H$ ($CDCl_3$, 400 MHz): 3.60 (2H, t, J=6.6 Hz, H-1), 2.66 (2H, t, J=6.9 Hz, H-10), 1.54 (2H, qn, J=7.0 Hz, H-9), 1.41 (2H, qn, J=6.9 Hz, H-2), 1.35-1.24 (12H, m, H-3-8)

$\delta_C$ ($CDCl_3$, 100 MHz): 63.0 (C-1), 42.3 (C-10), 33.9 (C-9), 32.9 (C-2), [29.5, 29.5, 29.4, 29.4, 26.9, 25.8 (Alk-$CH_2$)]

O-Benzyl-N-(10-hydroxydecyl) carbamate (12)

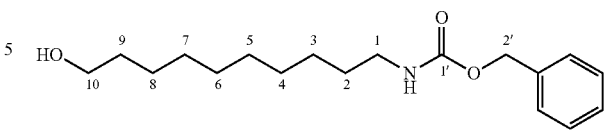

$Na_2CO_3$ (2.96 g, 27.9 mmol) and benzyl chloroformate (2.07 mL, 2.47 g, 14.5 mmol) was added to a solution of 10-amino-1-decanol (11) (1.93 g, 11.1 mmol) in $CH_2Cl_2$:$H_2O$ (1:1, 100 mL), which was stirred for 20 hrs. The organic layer was separated and aqueous layer extracted with $CH_2Cl_2$ (3×50 mL). The combined organic extracts were dried over $MgSO_4$, filtered and concentrated in vacuo to yield a crude solid which was purified using column chromatography (Hex:EtOAc 6:4, 5:5) to give the title compound as a white solid (3.13 g, 91%). $R_f$=0.35 (Hex:EtOAc 1:1), $\delta_H$ ($CDCl_3$, 400 MHz): 7.36-7.26 (5H, m, ArH), 5.10 (2H, s, H-2'), 4.70 (1H, b.s, —NH), 3.63 (2H, t, J=6.6 Hz, H-10), 3.18 (2H, m, H-1), 1.58-1.47 (4H, m, H-2/9), 1.30-1.20 (12H, m, H-3-8)

$\delta_C$ ($CDCl_3$, 100 MHz): 156.4 (C=O), [136.7, 128.5, 128.0 (ArC)], 66.6 (C-2'), 63.0 (C-10), 41.1 (C-1), 32.8 (C-9), 29.9 (C-2), [29.4, 29.4, 29.3, 29.2, 26.7, 25.7 (Alk$CH_2$)]

O-Cert-Butyl-N-(10-hydroxydecyl) carbamate (13)

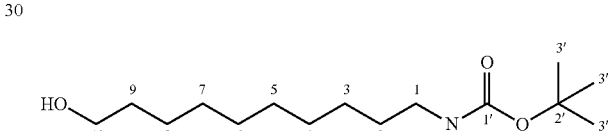

Di-tert-butyl dicarbonate (1.05 g, 4.8 mmol) dissolved in $CH_2Cl_2$ (5 mL) was added at 0° C. to a solution of 10-amino-1-decanol (11) (0.70 g, 4.0 mmol) in $CH_2Cl_2$:MeOH (4:1, 20 mL) and stirred for 2.5 hrs at 0-5° C. All the solvent was removed under vacuum and the white solid residue was purified using column chromatography (Hex:EtOAc 5:5; 4:6; 3:7) to give the title compound as a white solid (0.84 g, 76%). $R_f$=0.60 (Hex:EtOAc 4:6), $\delta_H$ ($CDCl_3$, 400 MHz): 4.51 (1H, b.s, —NH), 3.62 (2H, t, J=6.6 Hz, H-10), 3.08 (2H, m, H-1), 1.55 (2H, m, H-2), 1.46 (2H, m, H-9), 1.43 (9H, s, H-3'), 1.35-1.25 (12H, m, H-3-8)

O-Benzyl-N-(10-bromodecyl) carbamate (14)

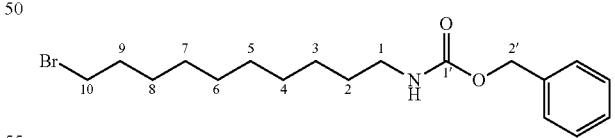

Triphenylphosphine (3.45 g, 13.15 mmol) and carbon tetrabromide (4.38 g, 13.15 mmol) were added to a solution of carbamate 12 (2.70 g, 8.77 mmol) in dry $CH_2Cl_2$ (160 mL) under $N_{2(g)}$, which was stirred for 3 hrs. Silica was added to the solution and the crude material was then dry loaded onto a prepacked column and purified using automated flash column chromatography (Hexane:EtOAc 9:1, 8.2). The title compound was obtained as a white solid (2.99 g, 92%). $R_f$=0.68 (Hex:EtOAc 1:1);

$\delta_H$ ($CDCl_3$, 300 MHz): 7.35-7.28 (5H, m, ArH), 5.09 (2H, s, H-2'), 4.75 (1H, b.s, —NH), 3.40 (2H, t, J=6.8 Hz, H-10), 3.18 (2H, m, H-1), 1.84 (2H, qn, J=6.8 Hz, H-9), 1.50-1.36 (4H, m, H-2, H-8), 1.33-1.20 (10H, m, Alk-CH$_2$)

$\delta_C$ (CDCl$_3$, 100 MHz): 156.4 (C=O), [136.7, 128.5, 128.3, 128.0 (Ar—C)], 66.5 (C-2'), 41.1 (C-1), 33.9 (C-10), 32.8 (C-9), 29.9 (C-2), [29.3, 29.3, 29.1, 28.7, 28.1, 26.7 (AlkC)]

O-tert-Butyl-N-(10-bromodecyl)carbamate (15)

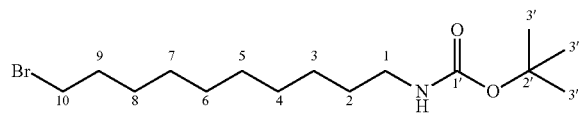 [SMILES: CC(C)(C)OC(=O)NCCCCCCCCCCBr]

Triphenylphosphine (0.623 g, 2.37 mmol) and carbon tetrabromide (0.787 g, 2.37 mmol) were added to a solution of carbamate 13 (0.500 g, 1.82 mmol) in dry CH$_2$Cl$_2$ (20 mL) under N$_{2(g)}$, which was stirred for 2.5 hrs. Silica was added to the solution and the crude material was then dry loaded onto a column and purified using column chromatography (Hexane:EtOAc 9:1, 8.2). The title compound was obtained as a white solid (0.56 g, 91%). R$_f$=0.65 (Hex:EtOAc 8:2);

$\delta_H$ (CDCl$_3$, 400 MHz): 4.49 (1H, b.s, —NH), 3.40 (2H, t, J=6.6 Hz, H-10), 3.09 (2H, m, H-1), 1.85 (2H, m, H-9), 1.46-1.38 (13H, m, H-2/8/3'), 1.33-1.25 (10H, m, H-3-7)

Example 4

Linker—Synthesis of Components for a Cleavable Linker S-(10-(((tert-butoxycarbonyl)amino)decyl) ethanethioate (16)

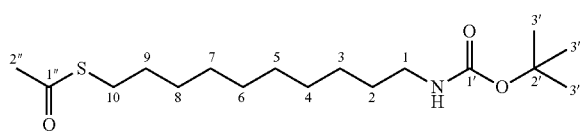 [SMILES: CC(=O)SCCCCCCCCCCNC(=O)OC(C)(C)C]

Thioacetic acid (0.078 g, 1.03 mmol) was added to a suspension of NaH (60% in mineral oil) (0.034 mg, 0.86 mmol) in anhydrous THF (5 mL) and stirred for 10 min. This solution was then added dropwise to a solution of carbamate 15 (0.290 mg, 0.86 mmol) in anh. THF (5.0 mL) under N$_{2(g)}$ at 0° C. and stirred overnight at RT°. All solvent was evaporated under vacuum and the residue redissolved in EtOAc (10 mL) followed by extraction with sat. NH$_4$Cl$_{(aq)}$ (2×15 mL). The organic phase was then washed with NaHCO$_3$ (15.0 mL) and brine (15.0 mL). The organic phase was dried, filtered and concentrated and the crude oil purified with column chromatography (Hex:EtOAc 9.5:0.5) to yield the title compound as a white solid (0.178 mg, 62%), R$_f$=0.40 (Hex:EtOAc 9:1)

$\delta_H$ (CDCl$_3$, 400 MHz): 4.49 (1H, b.s, —NH), 3.09 (2H, qt, J=6.0 Hz, H-1), 2.85 (2H, t, J=7.2 Hz, H-10), 2.31 (3H, s, H-2"), 1.56 (2H, qn, J=7.6 Hz, H-9), 1.46-1.40 (11H, m, H-2/3'), 1.35-1.26 (12H, m, H-3-8)

O-tert-butyl N-(10-mercaptodecyl)carbamate (17)

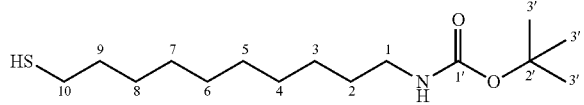

NaOMe (25% in MeOH)(0.05 mL) was added to a solution of thioacetate 16 (0.160 g, 0.48 mmol) in MeOH (2.0 mL) and stirred for 30 min. No starting material remained and so all solvent was evaporated and the residue redissolved in EtOAc followed by washing with NH$_4$Cl$_{(aq)}$. The organic phase was dried, filtered and concentrated and purified with column chromatography (Hex:EtOAc 9:1) to yield the title compound as a white solid (0.135 g, 98%) R$_f$=0.37 (Hex:EtOAc 9:1).

$\delta_H$ (CDCl$_3$, 400 MHz): 4.49 (1H, b.s, —NH), 3.09 (2H, qt, J=6.4 Hz, H-1), 2.51 (2H, qt, J=7.2 Hz, H-10), 1.59 (2H, qn, J=7.2 Hz, H-9), 1.46-1.40 (11H, m, H-2/3'), 1.36 (2H, m, H-8), 1.31 (1H, t, J=7.6 Hz), 1.27 (10H, m, H-3-7)

3-Bromopropyl-thiotosylate (18)

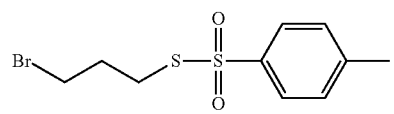

1,3-dibromopropane (3.56 g, 17.64 mmol) was added to a solution of potassium thiotosylate (1.00 g, 4.41 mmol) in MeCN (30.0 mL) under N$_2$ $_{(g)}$ and refluxed for 2 hrs. The reaction was then removed from the heat, allowed to cool and the solvent evaporated under vacuum. The residue was redissolved in CH$_2$Cl$_2$ (25.0 mL) and washed with water (3×20 mL) and brine (1×20 mL). The organic phase was then dried, filtered and concentrated followed by purification of the crude material with column chromatography (Hex:EtOAc 9:1). The title compound was obtained as a clear oil (1.02 g, 75%). R$_f$=0.35 (Hex:EtOAc 8:2).

Example 5

Pro-Conjugate—Synthesis by Attachment of Glucose Linker and Non-Cleavable Linker to Cyclam 1,4,8,11-Tetraazatricyclo[9.3.1.1]hexadecane (19)

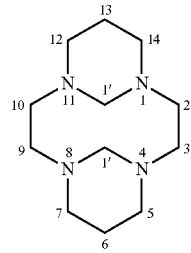

Formaldehyde (37% in H$_2$O) (0.75 mL, 10.0 mmol) was added to a solution of cyclam (1.00 g, 5.0 mmol) dissolved in water (20 mL) and cooled in an ice bath to 0-5° C. The solution was stirred for 5 min at that temperature after which it was allowed to warm to room temperature and stirred for 2.5 hrs. The reaction was cooled again to 0-5° C. and stirred for 5 min to maximise the precipitation of white solid which had formed which was then filtered off and washed with ice water (3×20 mL). The solid was dissolved in CH$_2$Cl$_2$ (25 mL) and MeOH (5 mL) and the solution dried over MgSO$_4$.

The MgSO$_4$ was filtered of and the solvent removed in vacuo to yield the title product as a white solid (1.05 g, 94%).

$\delta_H$ (CDCl$_3$, 400 MHz): 5.40 (2H, dt, J=3.0 Hz, 13.5 Hz, H-1'a), 3.14 (4H, m, H-2/3/9/10), 2.90 (2H, d, J=13.5 Hz, H-1'b), 2.85-2.80 (4H, m, H-5/7/12/14), 2.62 (4H, td, J=4.5 Hz, 15.5 Hz, H-5/7/12/14), 2.38 (4H, m, H-2/3/9/10), 2.28-2.18 (2H, m, H-6/13), 1.21-1.16 (2H, dqn, J=2 Hz, J=16.5 Hz, H-6/13), $\delta_C$ (CDCl$_3$, 100 MHz): 68.9 (C-1'), 53.6 (C-2/3/9/10), 49.3 (C-5/7/12/14), 20.3 (C-6/13)

1-[10-(Benzyloxycarbonylamino)decyl]-1,4,8,11-tetraaza-4,8-methano-cyclopentadecane ammonium bromide (20)

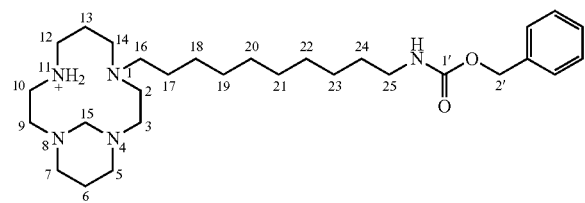 [SMILES: O=C(NCCCCCCCCCCN1CCCNCCN2CCCN(CC1)C2)OCc1ccccc1]

Bromide 15 (1.06 g, 2.88 mmol) was added under N$_{2(g)}$ to a solution of bridged cyclam 19 (0.773 g, 3.45 mmol) in anh. CH$_3$CN (80 mL) and stirred for 72 hrs in a flask wrapped with foil. The solvent was evaporated and the crude oil redissolved in CH$_2$Cl$_2$ (50 mL) and washed with H$_2$O (50 mL). The aqueous layer was extracted with CH$_2$Cl$_2$ (2×50 mL) and the organic layers combined, dried, filtered and concentrated. The residue obtained was purified with column chromatography (CH$_2$Cl$_2$:MeOH 9:1 with few drops of NH$_4$OH) to yield an oil (1.02 g, 69%), R$_f$=0.56 (CH$_2$Cl$_2$:MeOH 9:1)

$\delta_H$ (CDCl$_3$, 400 MHz): 12.70 (1H, bs, NH), 9.10 (1H, bs, NH), 7.31-7.24 (5H, m, ArH), 5.05 (2H, s, H-2'), 4.77 (1H, bs, NH), 4.05 (1H, d, J=12.0 Hz, H-15a), 3.68 (1H, m, CH$_2$N), 3.34 (1H, d, J=12.0 Hz, H-15b), 3.20-3.10 (4H, m, CH$_2$N, H-25), 3.05-2.83 (8H, m, CH$_2$N), 2.73 (1H, dt, J=5.0, 12.0 Hz, CH$_2$N), 2.43 (1H, m, H-16a), 2.35-2.25 (3H, m, H-16b, CH$_2$N), 2.20 (1H, m, CH$_2$N), 2.11 (2H, m, CH$_2$N, H-6a), 1.87 (1H, m, H-6b), 1.65 (1H, m, H-13a), 1.55 (1H, m, H-13b), 1.50-1.30 (4H, m, H-17/24), 1.28-1.20 (12H, m, CH$_2$Alk)

$\delta_C$ (CDCl$_3$, 100 MHz): 156.4 (C-1'), [136.6, 128.4, 128.0, 128.0 (ArC)], 72.8 (C-15), 66.5 (C-2'), 53.7 (C-16), [52.9, 49.3, 48.5, 48.1, 48.0, 48.0, 46.0, 45.1 (C—N)], 41.0 (C-25), 29.9 (C-17), 29.5, 29.5, 29.4, 29.1, 27.7, 26.6, 26.3, 25.1 (C-13), 22.4 (C-6)

1-[10-(2,3,4,6-O-Tetrabenzoyl-β,D-glucopyranos-1-yl)-1-oxodecyl]-11-[10-(benzyloxycarbonylamino)decyl]-1,4,8,11-tetraaza-4,8-methano-cyclopentadecane (21)

DMAP (0.046 g, 0.37 mmol) and Et$_3$N (0.190 g, 1.88 mmol) was added to a solution of cyclam derivative 20 (0.460 g, 0.93 mmol) dissolved in anh. THF (35 mL). Acid chloride 9 (0.775 g, 1.0 mmol) dissolved in anh. THF (7.8 mL) was added to the solution and stirred for 1.5 hrs. The solution was filtered through Celite to remove triethylammonium salts followed by the removal of THF in vacuo. The crude oil was redissolved in CH$_2$Cl$_2$ (20 mL) and extracted with H$_2$O (2×20 mL). The organic layer was washed with 2M NaOH (20 mL) and separated and the aqueous layer extracted with CH$_2$Cl$_2$ (2×20 mL). All organic phases were combined, dried, filtered and concentrated. The crude oil was purified using column chromatography (CH$_2$Cl$_2$:MeOH 9:1) to yield the title compound as an oil (0.76 g, 65%) R$_f$=0.45 (CH$_2$Cl$_2$:MeOH 9:1). HPLC analysis indicated that the one spot contained two inseparable compounds, which were the title compound as indicated and the same compound with no bisaminal bridge.

$\delta_H$ (CDCl$_3$, 300 MHz): 8.01-7.81 (8H, m, ArH), 7.52-7.25 (17H, m, ArH), 5.89 (1H, t, J=9.6 Hz, 3'), 5.65 (1H, t, J=9.6 Hz, H-4'), 5.50 (1H, dd, J=7.8, 9.6 Hz, H-2'), 5.08 (2H, s, H-2"), 4.83 (1H, d, J=7.8 Hz, H-1'), 4.80 (1H, bs, NH), 4.62 (1H, dd, J=3.2, 12 Hz, H-6'a), 4.50 (1H, dd, J=5.2, 12.0 Hz, H-6'b), 4.15 (1H, m, H-5'), 3.90 (1H, dt, J=6.4, 9.6 Hz, H-25a), 3.85-3.55 (3H, bm, —NCH$_2$), 3.53 (1H, dt, J=6.8, 9.6 Hz, H-25b), 3.41 (2H, bs, —NCH$_2$), 3.17 (2H, t, J=6.8 Hz, H-35), 2.78-2.45 (10H, bm, —NCH$_2$), 2.39-2.30 (5H, m, H-26/—NCH$_2$), 2.26 (2H, m, H-17), 1.70-1.38 (12H, m, H-18/24/27/34/6/13), 1.35-1.00 (22H, m, CH$_2$-alk), $\delta_C$ (CDCl$_3$, 100 MHz): 172.9 (C=O), [166.1, 165.8, 165.2, 165.0 (C=O)], 156.4 (C=O), 136.7 (ArC), [133.4, 133.2, 133.2, 133.1 (ArC)], [129.8, 129.8, 129.7, 129.5, 128.9, 128.9, 128.5, 128.5, 128.4, 128.4, 128.3, 128.3, 128.1 (ArC)], 101.3 (C-1'), 73.0 (C-3'), 72.1 (C-2'), 71.9 (C-5'), 70.7 (C-15), 70.3 (C-25), 69.9 (C-4'), 66.5 (C-2"), 63.3 (C-6'), 56.0 (C-26), [55.4, 55.0, 54.7, 54.4, 54.1, 53.9, 52.7, 52.4, 51.9, 51.1, 50.2, 46.5, 45.1, 43.7 (NCH$_2$)], 41.1 (C-35), 33.4/33.1 (C-17), 29.9 (C-34), 29.5, 29.5, 29.4, 29.4, 29.3, 29.2, 27.8, 27.6, 27.5, 26.9, 26.8, 25.7, 25.5, 21.6

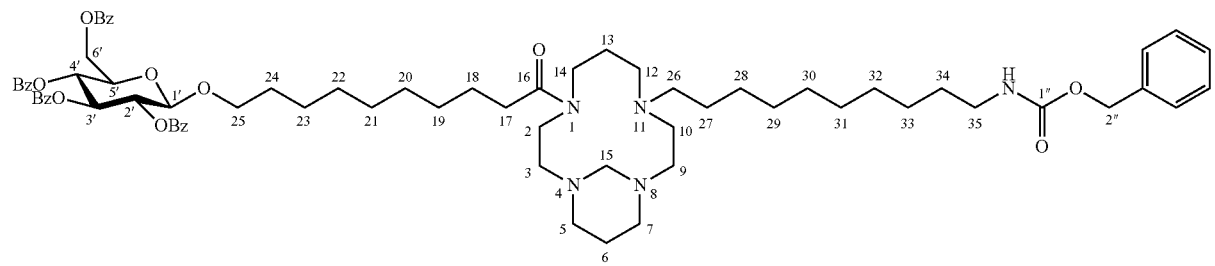

1-[10-(2,3,4,6-O-Tetrabenzoyl-β,D-glucopyranos-1-yl)-1-oxodecyl]-4,8-bis(tert-butoxycarbonylmethyl)-11-[10-(benzyloxycarbonylamino)decyl]-1,4,8,11-tetraazacyclotetradecane (22)

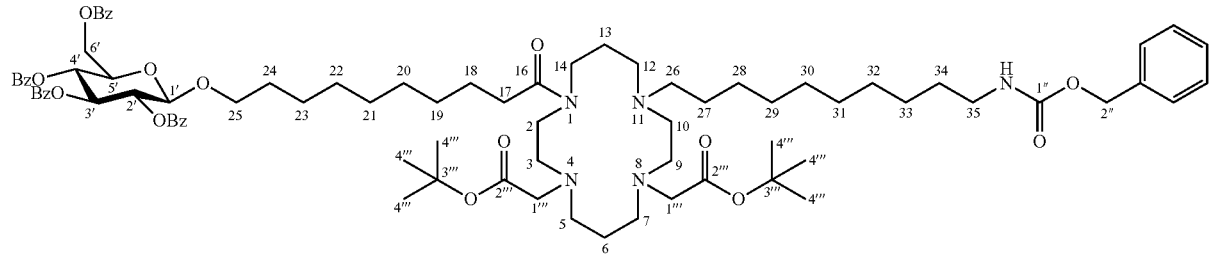

Potassium carbonate (0.033 g, 0.24 mmol) was added to a solution of cyclam 21 (0.100 g, 0.08 mmol) in anh. $CH_3CN$ (15 mL) under $N_{2(g)}$. t-Butylbromoacetate (0.047 g, 0.24 mmol) was dissolved in anh. $CH_3CN$ (1 mL) and added to the solution which was then stirred for 16 hrs. The solvent was removed on the rotary evaporator and the residue was redissolved in $H_2O$ (20 mL) and extracted with $CH_2Cl_2$ (4×20 mL). The organic extracts were dried, filtered and the solvent evaporated under vacuum. The oily residue was purified using column chromatography ($CH_2Cl_2$:MeOH 9.5:0.5) to yield the title compound as an oil (0.086 g, 73%).

$δ_H$ (CDCl$_3$, 400 MHz): 8.02-7.81 (8H, m, ArH), 7.53-7.25 (17H, m, ArH), 5.89 (1H, t, J=9.6 Hz, H-3'), 5.66 (1H, t, J=9.6 Hz, H-4'), 5.50 (1H, dd, J=7.8, 9.6 Hz, H-2'), 5.09 (2H, s, H-2''), 4.83 (1H, d, J=7.8 Hz, H-1'), 4.78 (1H, bs, NH), 4.63 (1H, dd, J=3.2, 12.0 Hz, H-6'a), 4.50 (1H, dd, J=5.2, 12.0 Hz, H-6'b), 4.15 (1H, m, H-5'), 3.90 (1H, dt, J=6.4, 9.6 Hz, H-25a), 3.53 (1H, dt, J=6.8, 9.6 Hz, H-25b), 3.45 (4H, m, NCH$_2$), 3.25 (2H, m, H-1'''), 3.22 (2H, s, H-1''''), 3.17 (2H, t, J=6.8 Hz, H-35), 2.82-2.62 (8H, m, H-26/NCH$_2$), 2.46 (2H, m, NCH$_2$), 2.37 (4H, m, NCH$_2$), 2.25 (2H, t, J=6.8 Hz, H-17), 1.67 (1H, bm, CH$_2$), 1.57 (5H, m, CH$_2$), 1.50 (4H, m, CH$_2$), 1.45 (9H, s, H-4''''), 1.43 (9H, s, H-4''''), 1.32-1.02 (24H, m, CH$_2$Alk)

$δ_C$ (CDCl$_3$, 100 MHz): 172.9 (C-16), 170.8 (C-2''''), [166.1, 165.8, 165.2, 165.0 (C=O)], 156.4 (C-1''), 136.7 (ArC), [133.3, 133.1, 133.1, 133.0, 129.8, 129.7 (×4), 129.4, 128.9 (×2), 128.5, 128.4, 128.3 (×3), 128.2, 128.0 (ArC)], 101.3 (C-1'), 80.6 (×2)(C-3''), 73.0 (C-3'), 72.2 (C-2'), 72.0 (C-5'), 70.3 (C-25), 70.0 (C-4'), 66.5 (C-2''), 63.3 (C-6'), 57.2 (C-1'''), 55.9, (C-1''''), [55.0, 53.9, 52.3, 52.0, 51.3, 51.2 (×2), 47.0, 44.9 (NCH$_2$)], 41.1 (C-35), 33.1/33.0 (0-17), [30.0, 29.5, 29.4 (×3), 29.3, 29.2 (×2), 28.2 (×2), 28.0, 27.6, 26.7 (×2), 26.5, 25.8, 25.5 (×3)(CH$_2$Alk, C-6/13, C-4''')]

1-[10-(β,D-glucopyranos-1-yl)-1-oxodecyl]-11-[10-(benzyloxycarbonylamino)decyl]-1,4,8,11-tetraaza-4,8-methanocyclopentadecane (23)

Sodium metal (0.119 g, 5.17 mmol) was reacted with anh. MeOH (5 mL) and then added to a solution of glucose-cyclam 21 (0.640 g, 0.512 mmol) in anh. MeOH (30 mL) under $N_{2(g)}$ and stirred for 1 hr. The MeOH was evaporated in vacuo and the product redissolved in $CH_2Cl_2$ (20 mL). Water (20 mL) was added for extraction upon which an emulsion formed. The emulsion was left to separate and the organic layer was removed followed by further extraction of the aqueous phase with DCM (3×40 mL) with a bit of MeOH (5 mL). The organic layers were combined, dried, filtered and concentrated. The crude oil was dry-loaded and purified using automated column chromatography ($CH_2Cl_2$:MeOH:NH$_4$OH, 8:1.8:0.2) to yield the title product as an oil (0.374 g, 92%). $R_f$=0.55 ($CH_2Cl_2$:MeOH:NH$_4$OH, 8:1.8:0.2)

$δ_H$ (CD$_3$OD, 400 MHz): 7.34-7.23 (5H, m, ArH), 5.06 (2H, s, H-2''), 4.25 (1H, d, J=7.8 Hz, H-1'), 3.91-3.84 (2H, m, H-6'a/25a), 3.80-3.55 (2H, bm, —NCH$_2$ including 3.67 (1H, m, H-6'b)), 3.60-3.40 (2H, bs, —NCH$_2$ including 3.53 (1H, dt, J=6.9, 9.6 Hz, H-25b)), 3.37-3.23 (5H, m, H-3'/4'/NCH$_2$), 3.17 (1H, t, J=7.8 Hz, H-2'), 3.10 (2H, t, J=7.2 Hz, H-35), 2.80-2.50 (10H, bm, —NCH$_2$), 2.50-2.40 (4H, m, H-26/NCH$_2$), 2.37 (2H, t, J=7.2 Hz, H-17), 1.74 (2H, m), 1.61 (4H, m), 1.48 (4H, m), 1.40-1.20 (24H, m, CH$_2$-alk)

$δ_C$ (CD$_3$OD, 100 MHz): 175.6 (C=O), 158.8 (C=O), 138.5 (ArC), [129.4, 128.9, 128.7 (ArC)], 104.4 (C-1'), 78.1 (C-3'), 77.9 (C-2'), 75.1 (C-5'), 71.7 (C-25), 71.1 (C-15), 70.9 (C-4'), 67.2 (C-2'), 62.8 (C-6'), 56.9 (C-26), [56.2, 55.4, 55.2, 55.2, 54.6, 54.5, 54.5, 53.8, 53.1, 52.5, 51.1, 51.1, 47.9, 46.0, 45.1, 42.3 (NCH$_2$)], 41.8 (C-35), 34.2/34.0 (C-17), [30.9, 30.8, 30.6, 30.6, 30.5, 30.5, 30.4, 30.4, 28.7, 28.6, 28.1, 28.0, 27.8, 27.0, 26.8, 26.7, 22.4 (C-alk including C-6/13)]

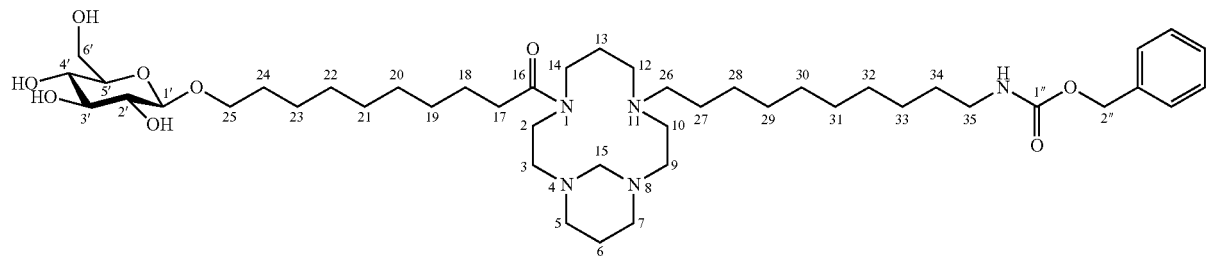

1-[10-(β,D-glucopyranos-1-yl)-1-oxodecyl]-11-[10-aminodecyl]-1,4,8,11-tetraazacyclotetradecane (24)

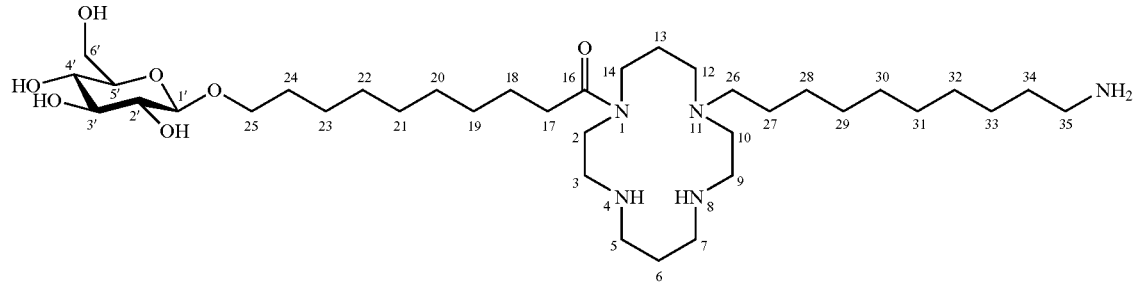

Pd/C (0.037 g, 10% w/w) was added to a solution of glucose cyclam 23 (0.374 g, 0.45 mmol) in anh. MeOH (10 mL). The flask was flushed with $H_{2(g)}$ and stirred overnight under a $H_{2\ (g)}$ environment using a hydrogen-filled balloon. The solution was filtered through a Celite pad which was washed with MeOH and the MeOH then removed under vacuum. The crude oil was then redissolved in MeOH (5 mL) and 2M NaOH (5 mL) added to obtain the product in its free base form. The water and MeOH were removed under vacuum and MeOH (10 mL) again added to the flask. A white solid precipitated out which was then filtered off though Celite. The solvent was evaporated and the crude product dry loaded and purified using column chromatography ($CH_2Cl_2$:MeOH:$NH_4OH$, 7:2.5:0.5). Two major isomers were obtained which could not be fully separated (top isomer 0.040 g, mixed isomers 0.153 g, bottom isomer 0.084 g, total yield=89%). NMR analysis indicated that the top isomer still contained the bis-aminal bridge whereas the bottom isomer was analysed to be the title compound.

$\delta_H$ ($CD_3OD$, 400 MHz): 4.25 (1H, d, J=8.0 Hz, H-1'), 3.89 (1H, dt, J=6.8, 9.6 Hz, H-25a), 3.86 (1H, dd, J=2.0, 12.0 Hz, H-6'a), 3.68 (1H, dd, J=5.6, 12.0 Hz, H-6'b), 3.62-3.44 (5H, m, H-2/14/25b), 3.37 (1H, t, J=8.8 Hz, H-3'), 3.32-3.24 (2H, m, H-4'/5'), 3.17 (1H, t, J=8.0 Hz, H-2'), 2.96 (2H, m, —$NCH_2$), 2.86-2.76 (8H, m, H-35/—$NCH_2$ (×3)), 2.66 (2H, m, —$NCH_2$), 2.55-2.33 (6H, m, H-17/26/$NCH_2$), 1.85 (2H, m, H-6), 1.80-1.55 (8H, m, H-13/18/24/34), 1.49 (2H, m, H-27), 1.42-1.28 (22H, m, $CH_2$-alk)

$\delta_C$ ($CD_3OD$, 100 MHz): 175.6 (C-16), 104.4 (C-1'), 78.2 (C-3'), 77.9 (C-2'), 75.2 (C-5'), 71.8 (C-25), 70.9 (C-4'), 62.9 (C-6'), 56.0 (C-26), [53.5, 53.4, 52.8, 52.6, 51.3 (×2), 50.5 (×2), 49.7 (×2), 48.6 (×2), 48.0 (×2), 46.4 (×2) ($NCH_2$ and rotamer)], 41.4 (C-35), 34.2/33.9 (C-17 and rotamer), [30.8, 30.6 (×2), 30.4 (×2), 30.4, 30.3, 28.7, 28.5, 28.2, 27.8, 27.6, 27.4, 27.0, 26.7 ($CH_2$Alk including C-6/13 and rotamers)]

1-[10-(2,3,4,6-O-Tetrabenzoyl-(β,D-glucopyranos-1-yl)]-4,11-bis(tert-butoxycarbonylmethyl)-1,4,8,11-tetraazacyclotetradecane (25)

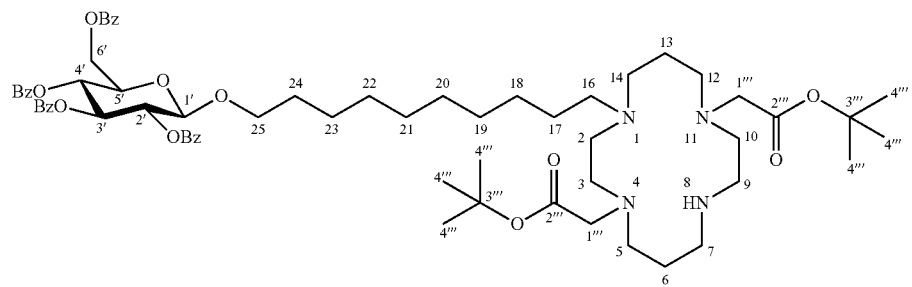

Bromide 4 (0.126 g, 0.16 mmol) was dissolved in $CH_3CN$ (5 mL) and added under $N_{2(g)}$ to a solution of 1,8-bis(t-butoxycarbonylmethyl)-1,4,8,11-tetraazacyclotetradecane (0.095 g, 0.22 mmol) in anh. $CH_3CN$ (5 mL) with $K_2CO_3$ (0.061 g, 0.44 mmol) and stirred for 72 hrs at 60° C. The solvent was evaporated and the crude oil redissolved in 1 M HCl (10 mL) and extracted with EtOAc (2×20 mL). The organic layers were combined, dried, filtered and concentrated and the residue was purified with column chromatography ($CH_2Cl_2$:MeOH 9.6:0.4; 9.4:0.6; 9.2:0.8; 9:1) to yield an oil (0.05 g, 28%), $R_f$=0.45 ($CH_2Cl_2$:MeOH 9:1).

$\delta_H$ ($CDCl_3$, 400 MHz): 8.00-7.81 (8H, m, ArH), 7.53-7.25 (17H, m, ArH), 5.88 (1H, t, J=9.6 Hz, H-3'), 5.65 (1H, t, J=9.6 Hz, H-4'), 5.50 (1H, dd, J=7.8, 9.6 Hz, H-2'), 4.82 (1H, d, J=7.8 Hz, H-1'), 4.61 (1H, dd, J=3.2, 12.0 Hz, H-6'a), 4.50 (1H, dd, J=5.2, 12.0 Hz, H-6'b), 4.15 (1H, m, H-5'), 3.89 (1H, dt, J=6.4, 9.6 Hz, H-25a), 3.63 (2H, m, $NCH_2$), 3.52 (1H, dt, J=6.8, 9.6 Hz, H-25b), 3.46 (2H, m, $NCH_2$), 3.32 (2H, m, $NCH_2$), 3.24-3.17 (2H, m, $NCH_2$), 3.16-3.08 (4H, m, $NCH_2$), 3.01 (2H, m, $NCH_2$), 2.92 (2H, m, $NCH_2$), 2.83 (2H, m, $NCH_2$), 2.74 (2H, m, $NCH_2$), 2.63 (2H, t, J=6.8 Hz, H-16), 2.05 (2H, m, H-6), 1.85 (2H, m, H-13), 1.53 (2H, m, $CH_2$), 1.47 (9H, s, H-4'''), 1.43 (9H, s, H-4'''), 1.32-1.02 (12H, m, $CH_2$Alk)

1-[10-(2,3,4,6-O-Tetrabenzoyl-β,D-glucopyranos-1-yl)]-4,11-bis(tert-butoxycarbonylmethyl)-8-[10-(t-butoxycarbonylamino)decyl]-1,4,8,11-tetraazacyclotetradecane (26)

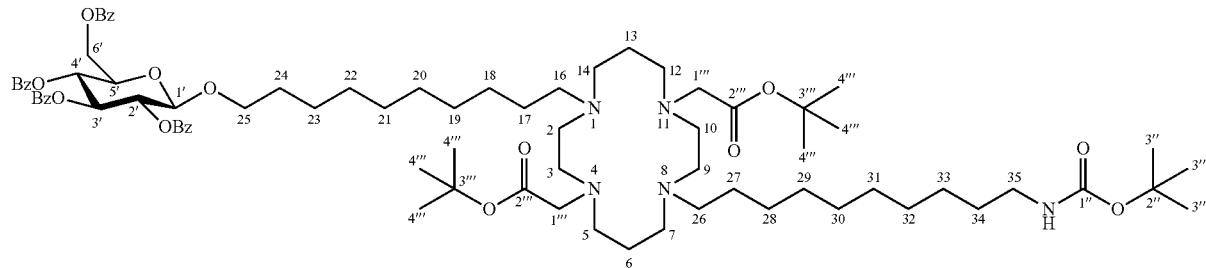

Bromide 15 (0.029 g, 0.08 mmol) was added under $N_{2(g)}$ to a solution of cyclam 25 (0.050 g, 0.04 mmol) in anh. $CH_3CN$ (2 mL) with $K_2CO_3$ (0.018 g, 0.12 mmol) and stirred for 24 hrs at 60° C. The reaction was proceeding very slowly and so extra bromide 15 (0.019 g) and $K_2CO_3$ (0.012 g) was added and the reaction again stirred for 24 hrs at 60° C. The solvent was evaporated and the crude oil was redissolved in 1 M HCl (10 mL) and extracted with EtOAc (3×10 mL). The organic layers were combined, dried, filtered and concentrated and the residue was purified with column chromatography ($CH_2Cl_2$:MeOH 9.5:0.5 with few drops of AcOH) to yield an oil (0.03 g, 50%), $R_f$=0.59 ($CH_2Cl_2$:MeOH 9.5:0.5).

1-[10-(β,D-glucopyranos-1-yl)]-4,11-diacetic acid-8-[10-aminodecyl]-1,4,8,11-tetraazacyclo tetradecane (27)

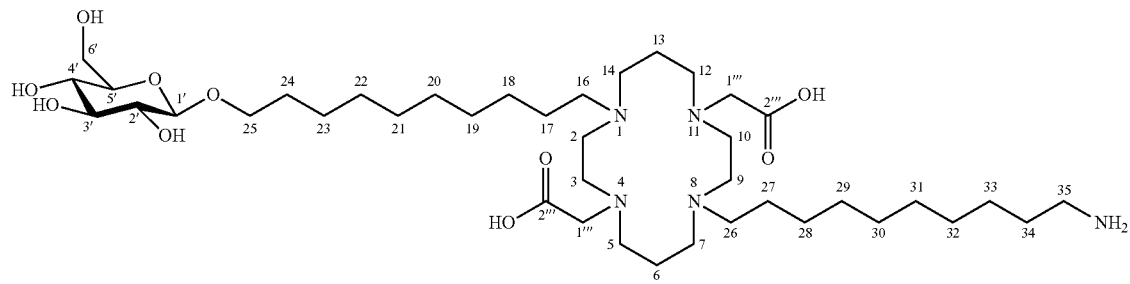

TFA (1.0 mL) was added to a solution of cyclam 26 (0.030 g, 0.02 mmol) in anh. MeOH (4 mL) to make a final solution of 20% TFA. The reaction was stirred for 24 hrs at room temperature. The solvent and TFA was evaporated under vacuum to yield a residue which was used directly in the next reaction. The residue was dissolved in MeOH (2 mL) and was stirred for 5 min after addition of NaOMe (24% in MeOH)(0.5 mL). The reaction was quenched with the addition of Dowex $H^+$ (0.5 g) and stirred for 5 min after which the Dowex was filtered off through a celite pad. The filtrate was concentrated to yield a solid residue to which MeOH (1 mL) was added to extract the product from the TFA salts. The MeOH was evaporated to yield a glassy solid (0.021 g) which still contained some TFA salt.

LRMS: m/z calculated for $C_{40}H_{79}N_5O_{10}$=789.58; found $(M+H^+)$=790.6

Example 6

Pro-Conjugate—Synthesis by Attachment of Glucose Linker and Cleavable Linker to Cyclam 1-[10-(β,D-glucopyranos-1-yl)]-4,11-bis(tert-butoxycarbonylmethyl)-1,4,8,11-tetraazacyclo-tetradecane (28)

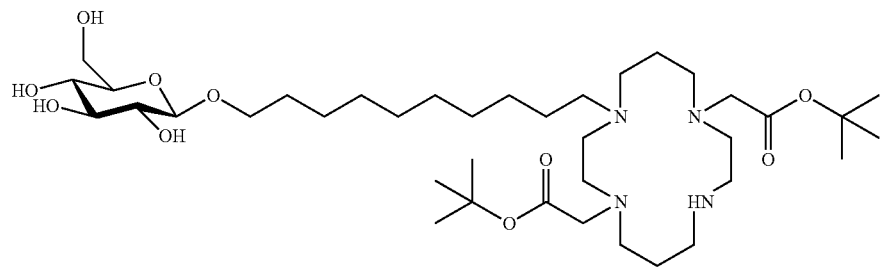

Sodium methoxide (0.20 mL, 25% solution) is added to a solution of cyclam 25 (0.05 g, 0.04 mmol) in anh. MeOH (2.0 mL) and stirred for 30 min. The solvent is evaporated and the residue is redissolved in EtOAc (5 mL) and washed with 0.25 M HCl (2×5 mL). The organic phase is dried, filtered, concentrated and purified by column chromatography (CH$_2$Cl$_2$:MeOH 8.5:1.5) to yield the title compound as an oil.

1-[10-(β,D-glucopyranos-1-yl)]-4,11-bis(tert-butoxycarbonylmethyl)-8-[3-(tosylthio)propyl]-1,4,8,11-tetraazacyclotetradecane (29)

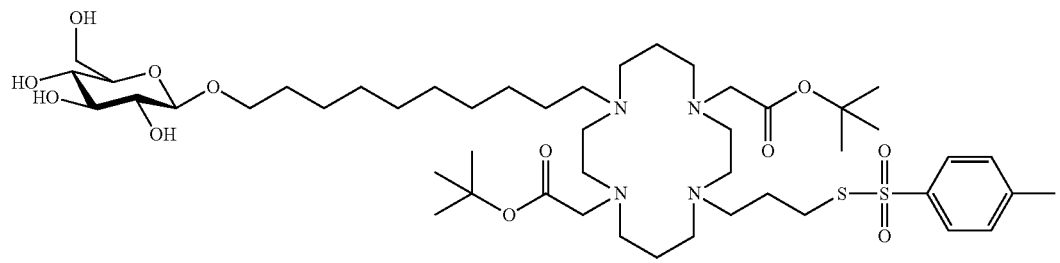

Bromide 18 (0.019 g, 0.06 mmol) is added under N$_{2(g)}$ to a solution of cyclam 28 (0.020 g, 0.03 mmol) in anh. CH$_3$CN (2 mL) with K$_2$CO$_3$ (0.012 g, 0.09 mmol) and stirred for 24 hrs at 60° C. The reaction is not quenched but proceeded directly to the next step.

1-[10-(β,D-glucopyranos-1-yl)]-4,11-bis(tert-butoxycarbonylmethyl)-8-[3-(pent-4-yn-1-yldisulfanyl)propyl]-1,4,8,11-tetraazacyclotetradecane (30)

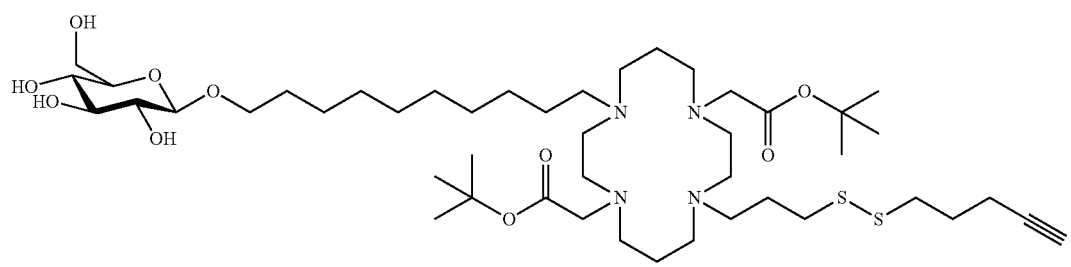

4-Pentyne-1-thiol (0.004 g, 0.04 mmol) is added to the previous reaction solution which is then refluxed for a further 2 hrs. The solvent is evaporated under vacuum and the crude residue was redissolved in EtOAc (5 mL) and washed with sat. aq. NH$_4$Cl (5 mL). The organic phase is dried, filtered, concentrated and purified with column chromatography (CH$_2$Cl$_2$:MeOH 9:1) to yield the title compound as an oil.

1-[10-(β,D-glucopyranos-1-yl)]-4,11-bis(tert-butoxycarbonylmethyl)-8-[3-((((tert-butoxycarbonyl)amino)decyl)disulfanyl)propyl]-1,4,8,11-tetraazacyclotetradecane (31)

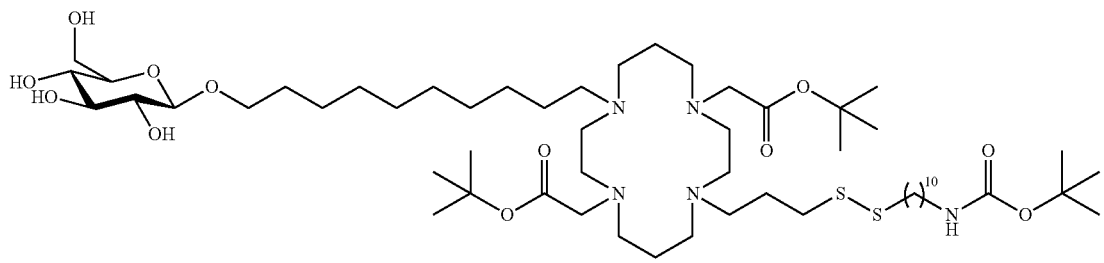

Thiol 17 (0.011 g, 0.04 mmol) is added to the solution from reaction 29 and is then refluxed for a further 2 hrs. The solvent is evaporated under vacuum and the crude residue is redissolved in EtOAc (5 mL) and washed with sat. aq. NH$_4$Cl (5 mL). The organic phase is dried, filtered, concentrated and purified with column chromatography (CH$_2$Cl$_2$:MeOH 9:1) to yield the title compound as an oil.

1-[10-(β,D-glucopyranos-1-yl)]-4,11-(diacetic acid)-8-[3-((aminodecyl)disulfanyl)propyl]-1,4,8,11-tetraazacyclotetradecane (32)

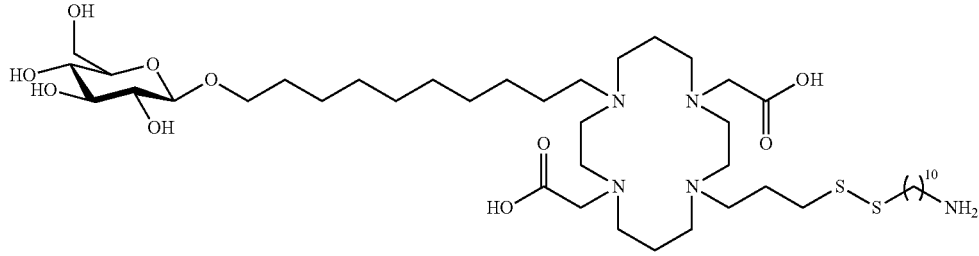

A solution of 6 M HCl/EtOAc (0.50 mL) is added to Cyclam 31 (0.020 g, 0.02 mmol) dissolved in EtOAc (4.5 mL) and stirred for 2 hrs. The product precipitated out as a white HCl salt which is then filtered off, washed once with EtOAc (5 mL) and dried.

1-[10-(β,D-glucopyranos-1-yl)]-4,11-(diacetic acid)-8-[3-(pent-4-yn-1-yldisulfanyl)propyl]-1,4,8,11-tetraazacyclotetradecane (33)

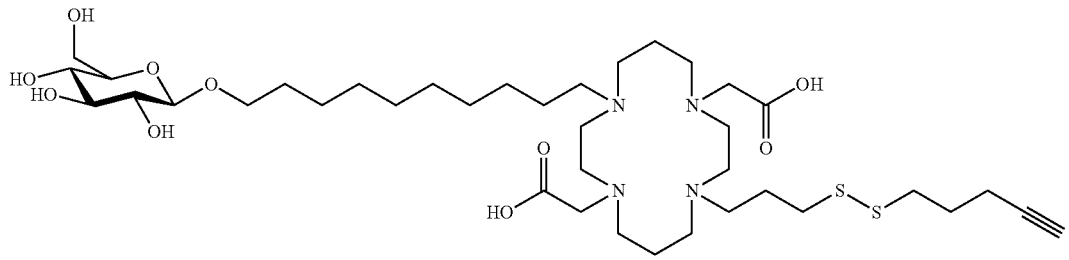

A solution of 6 M HCl/EtOAc (0.50 mL) is added to Cyclam 30 (0.020 g, 0.02 mmol) dissolved in EtOAc (4.5 mL) and stirred for 2 hrs. All solvent is evaporated off under vacuum and the solid product was recrystallised from EtOH.

Example 7

Radiolabelling—Synthesis and Radiolabelling of a Glucose-Cyclam Intermediate for Proof of Principle of $^{103}$Pd Co-Ordination 1,4,8-Tris-(tert-butoxycarbonylmethyl)-1,4,8,11-tetraazacyclotetradecane (34)

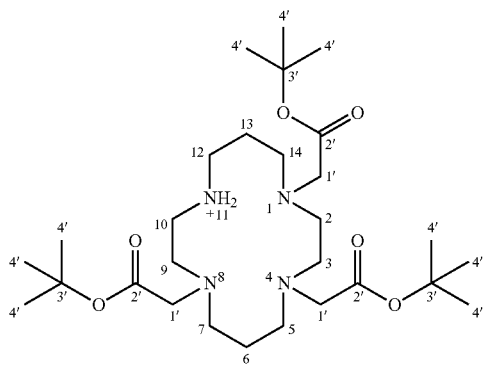 [SMILES: CC(C)(C)OC(=O)CN1CCCN(CC(=O)OC(C)(C)C)CCN(CC(=O)OC(C)(C)C)CCCNCC1]

t-Butylbromoacetate (0.205 g, 1.05 mmol) dissolved in CH$_3$CN (25 mL) was added to a solution of cyclam (0.100 g, 0.50 mmol) and NaHCO$_3$ (0.088 g, 1.05 mmol) in CH$_3$CN (70 mL) and refluxed for 15 hrs. The white precipitate that formed was filtered off and the solvent was removed in vacuo. The residue was then purified with column chromatography (CH$_2$Cl$_2$:MeOH:NH$_4$OH 10:1:0.1) to give the title compound as a slightly yellow oil which crystallised. The solid was recrystallised with toluene to yield clear crystals (0.126 g, 46%). δ$_H$ (CDCl$_3$, 400 MHz): 9.01 (2H, bs, —NH), 3.42 (2H, s, H-1'), 3.38 (2H, s, H-1'), 3.29 (2H, m, H-12), 3.17 (2H, m, H-9), 3.11 (2H, s, H-1'), 3.03 (2H, m, H-10), 2.74 (2H, t, J=5.6 Hz, CH$_2$N), 2.70 (2H, m, CH$_2$N), 2.63 (2H, t, J=5.6 Hz, CH$_2$N), 2.59 (4H, m, CH$_2$N), 2.03 (2H, bm, H-13), 1.66 (2H, m, H-6), 1.46 (9H, s, H-4'), 1.45 (9H, s, H-4'), 1.43 (9H, s, H-4')

δ$_C$ (CDCl$_3$, 100 MHz): 171.1 (C=O), 170.8 (C=O), 170.5 (C=O), 82.3 (C-3'), 81.6 (C-3'), 81.2 (0-3'), 55.8 (C-1'), 55.7 (C-1'), 55.3 (C-1'), 53.8 (CH$_2$N), 52.0 (C-12), 51.2 (C-9), 50.5 (CH$_2$N), 49.2 (CH$_2$N), 48.5 (C-10), 47.6 (CH$_2$N), 46.7 (CH$_2$N), 28.2 (C-4'), 23.3 (C-6), 22.5 (C-13)

1-(10-(tetra-O-benzoyl-β-D-glucopyranos-1-yl)decyl)-4,8,11-Tris-(tert-butoxycarbonylmethyl)-1,4,8,11-tetraazacyclotetradecane (35)

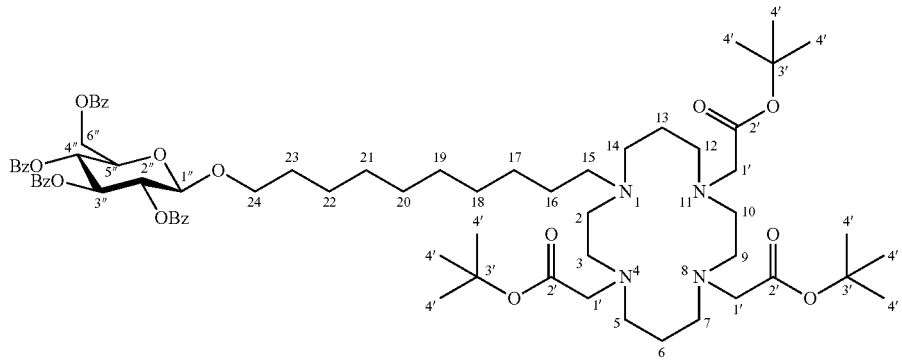

Bromide 4 (0.590 g, 0.72 mmol) was dissolved in anh. MeCN (10 mL) and added to a solution of cyclam 34 (0.327 g, 0.60 mmol) and NaHCO₃ (0.152 g, 1.80 mmol) in MeCN (50 mL). The reaction was refluxed at 80° C. for 48 hrs after which H₂O (1 mL) was added and the reaction again refluxed for 48 hrs. The solvent was evaporated under vacuum and the crude material redissolved in DCM (20 mL) and water (20 mL). The aqueous phase was extracted with DCM (3×20 mL) and the organic phase dried, filtered and concentrated to yield a crude oil which was purified with column chromatography using DCM:MeOH (9.5:0.5) as the mobile phase. The title product was obtained as a clear oil (0.370 g, 48%). δ$_H$ (CDCl₃, 300 MHz): 8.02-7.81 (8H, m, ArH), 7.55-7.25 (12H, m, ArH), 5.89 (1H, t, J=9.6 Hz, H-3"), 5.66 (1H, t, J=9.6 Hz, H-4"), 5.51 (1H, dd, J=7.8, 9.7 Hz, H-2"), 4.83 (1H, d, J=7.8 Hz, H-1"), 4.63 (1H, dd, J=3.4, 12.1 Hz, H-6a"), 4.50 (1H, dd, J=5.2, 12.1 Hz, H-6b"), 4.15 (1H, m, H-5"), 3.90 (1H, dt, J=6.2, 9.7 Hz, H-24a), 3.53 (1H, dt, J=6.2, 9.7 Hz, H-24b), 3.53 (2H, m, CH₂N), 3.32-3.22 (8H, m, CH₂N, 3×H-1'), 3.12-3.06 (4H, m, H-15, CH₂N), 2.72-2.60 (10H, m, 5×CH₂N), 1.99 (2H, m, H-13), 1.78 (2H, m, H-16), 1.61 (2H, m, H-6), 1.52 (2H, m, H-23), 1.45 (27H, s, H-4'), 1.30-1.05 (12H, m, CH₂-alk)

δ$_C$ (CDCl₃, 100 MHz): 170.7 (C-2'), 170.5 (C-2'), 170.7 (C-2'), [166.1, 165.8, 165.2, 165.0 (C=O)], [133.3, 133.1, 133.1, 133.0, 129.8 (×2), 129.7 (×4), 129.6 (×2), 129.4 (×2), 128.9 (×2), 128.4 (×4), 128.3 (×2), 128.2 (×2)(ArC)], 101.3 (C-1"), 81.4 (C-3'), 81.4 (C-3'), 81.0 (C-3'), 73.0 (C-3"), 72.1 (C-2"), 72.0 (C-5"), 70.3 (C-24), 69.9 (C-4"), 63.3 (C-6"), 55.7 (C-1'), 55.7 (C-1'), 55.2 (C-1'), 53.2 (C-15), [52.1, 51.9, 51.8, 51.0, 50.7, 50.2, 50.0, 49.6 (CH₂N)], [29.3, 29.3, 29.2, 29.1, 29.0 (CH₂)], 28.2 (×3)(C-4'), 26.9 (C-22), 25.7 (C-17), 25.4 (C-6), 23.4 (C-16), 22.5 (C-13)

1-(10-(β-D-glucopyranos-1-yl)decyl)-4,8,11-Tris-(acetic acid)-1,4,8,11-tetraazacyclotetra-decane trifluoroacetate salt (36)

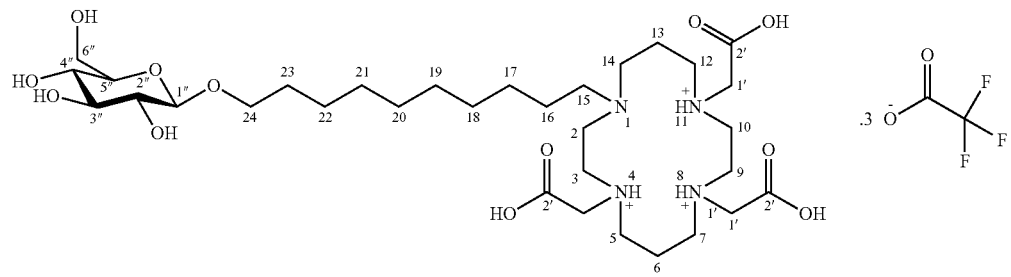

Sodium methoxide (0.20 mL, 25% solution) was added to a solution of cyclam 35 (0.110 g, 0.09 mmol) in anh. MeOH (4.0 mL) and stirred for 1 hr. The reaction was quenched with 0.25 M HCl (10 mL) and extracted with DCM (3×10 mL). The aqueous phase was basified to pH 10-11 with 2 M NaOH and again extracted with DCM (3×10 mL). The organic phase was dried, filtered and concentrated to yield a crude oil. This oil was then dissolved in DCM (2 mL) and trifluoroacetic acid (2.0 mL) added to the solution which was then stirred overnight. All solvent was then evaporated and the remaining oil redissolved in water (5 mL) and extracted with CHCl₃ (3×3 mL). The aqueous phase was concentrated down and further dried under high vacuum to yield the TFA-salt of the title compound as a glassy solid (0.032 g, 36%)

δ$_H$ (D₂O, 400 MHz): 4.32 (1H, d, J=7.8 Hz, H-1"), 3.93 (2H, s, H-1'), 3.79 (2H, m, H-6"a/24a), 3.61-3.51 (6H, m, H-6"b/24b/1"(×2)), 3.40-3.25 (11H, m, H-3"/4"/5"/NCH₂ (×4)), 3.16-3.08 (7H, m, H-2"/15/NCH₂ (×2)), 2.90 (4H, bm, —NCH₂ (×2)), 1.93 (4H, m, H-6/13), 1.59 (2H, m, H-16), 1.50 (2H, m, H-23), 1.25-1.15 (12H, m, CH₂-alk (×6))

δ$_C$ (D₂O, 100 MHz): 173.8 (C-2'), 173.7 (C-2'), 169.6 (C-2'), 102.1 (C-1"), 75.8 (C-3"), 75.8 (C-5"), 73.1 (C-2"), 70.6 (C-24), 69.9 (C-4"), 60.8 (C-6"), 54.7 (C-1'), 54.5 (C-1'), 54.4 (C-1'), 53.9 (C-15), [52.9, 52.5, 51.6, 51.5, 50.6, 50.0, 49.6, 48.9 (CH₂N)], [28.7, 28.4, 28.3, 28.3, 28.0, 25.6, 24.9 (CH₂)], 22.5 (C-16), [21.6, 21.0 (C-6/13)]

Procedure for Labelling Cyclam X with [103]Pd

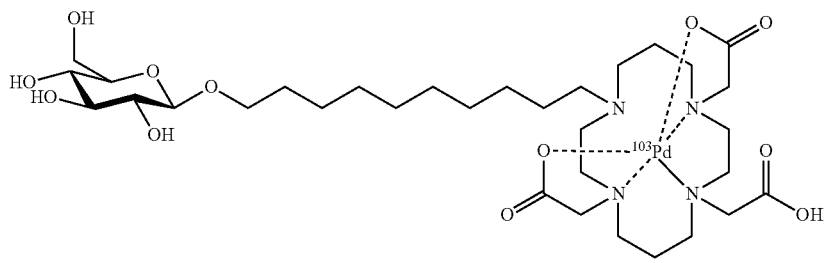

[103]Pd(NH$_3$)$_4$Cl$_2$ was dissolved in water (150 uL)(approx. pH 5) and the pH adjusted to 10-11 with 5M NaOH (4 uL). Cyclam 36 (50 uL 0.450 mg) was added to the [103]Pd(NH$_3$)$_4$Cl$_2$ solution in and the mixture heated at 80° C. for 30 min. The reaction solution (20 uL) was then analysed by injection into a HPLC fitted with a Agilent Zorbax Extend C-18 5um, 4.6×250 mm column and a Raytest Gabi Star Gamma detector and analysed with a mobile phase system of A: 0.01 M ammonium acetate pH 9.5, B: methanol run under a gradient elution (0 min A:B=95:5; 2 min A:B=80:20; 4 min A:B=50:50; 10 min A:B=0:100) with a flow rate of 0.8 mL/min. Free metal eluted at retention time of 1.35 min while labelled product had a retention time of 6.6 min.

Example 8

Radiolabelling—Radiolabelling of a Cyclam Pro-Conjugate 27 for Proof of Principle of [103]Pd Co-Ordination

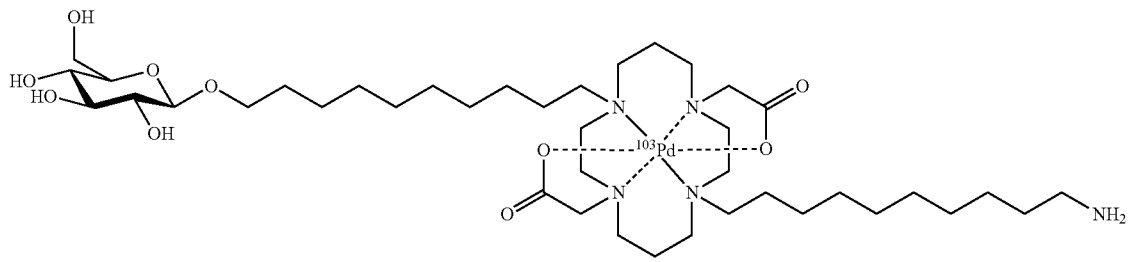

[103]Pd(NH$_3$)$_4$Cl$_2$ fraction (32 MBq) obtained from [103]Pd purification on anion exchange column was dissolved in milliQ-water (200 uL)(approx. pH 4). Cyclam 27 (100 uL, 1.0 mg) was added to the [103]Pd(NH$_3$)$_4$Cl$_2$ solution (100 uL) in a vial and the mixture heated at 85° C. for 30 min. The reaction solution (20 uL) was then analysed by injection into a HPLC fitted with a Agilent Zorbax Extend C-18 5 um, 4.6×250 mm column and a Raytest Gabi Star Gamma detector and analysed with a mobile phase system of A: 0.01 M ammonium acetate pH 9.5, B: methanol run under a gradient elution (0 min A:B=95:5; 2 min A:B=80:20; 4 min A:B=50:50; 10 min A:B=0:100) with a flow rate of 0.8 mL/min. Free metal eluted at retention time of 1.35 min while labelled product had a retention time of 7.9 min.

Example 9

Conversion of an Amine to a Maleimide Moiety
N-(Methoxycarbonyl)maleimide (37)

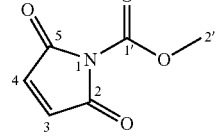

Methyl chloroformate (0.87 mL, 11.3 mmol) was added slowly to a solution of maleimide (1.00 g, 10.3 mmol) and N-methyl morpholine (1.24 mL, 11.3 mmol) in EtOAc (80 mL) at 0° C. and stirred for 1 hr. The precipitate was separated out through filtration through a celite pad and the filtrate concentrated in vacuo. It was attempted to recrystallise the crude oil with hexane:CH$_2$Cl$_2$ but no crystallisation occurred. The crude product was redissolved in EtOAc (100 mL), adsorbed onto silica and purified using column chromatography (Hex:EtOAc 6:4) to yield a white solid (1.07 g, 67%).

δ$_H$ (CDCl$_3$, 300 MHz): 6.83 (2H, s, CH-3/4), 3.94 (3H, s, CH$_3$-2')

δ$_C$ (CDCl$_3$, 100 MHz): 165.6 (C-2/5), 148.1 (C-1'), 132.3 (C-3/4), 54.2 (C-2')

N-10-(β-D-glucopyranos-1-yl)decyl-maleimide (38)

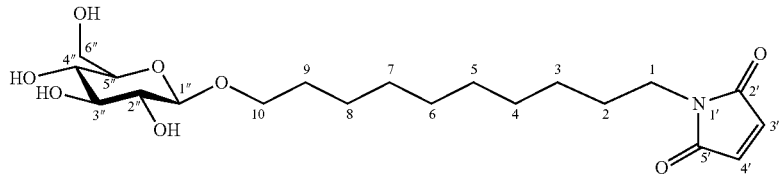

N-(methoxycarbonyl) maleimide (37) (0.014 g, 0.09 mmol) was added at RT to a stirring solution of (10-Aminodecyl) β-D-glucopyranoside (0.015 g, 0.04 mmol) in dioxane (0.75 mL) and sat. NaHCO$_3$ $_{(aq)}$ (1.5 mL). The reaction was stirred for 1 hr after which the reaction was quenched with EtOAc (10 mL) and water (10 mL). The organic phase was separated out and the aq. phase extracted with EtOAc (3×10 mL). The organic layers were combined, dried, filtered and the solvent evaporated under vacuum. The residue was adsorbed onto silica and purified with column chromatography (CH$_2$Cl$_2$:MeOH 9:1). The title compound was obtained as a clear oil (0.011 g, 60%) Rf=0.15 (CH$_2$Cl$_2$: MeOH 9:1)

$\delta_H$ (CD$_3$OD, 300 MHz): 6.79 (2H, s, 3'/4'), 4.24 (1H, d, J=7.5 Hz, H-1"), 3.93-3.84 (2H, m, H-6"a/H-10a), 3.69-3.64 (1H, m, H-6"b), 3.57-3.50 (1H, dt, J=6.6, 9.6 Hz, H-10b), 3.48 (2H, t, J=6.9 Hz, H-1), 3.38-3.22 (3H, m, H-3"/4"/5"), 3.19-3.13 (1H, m, H-2"), 1.64-1.54 (4H, m, H-2/9), 1.42-1.28 (12H, m, AlkCH$_2$). $\delta_C$ (CD$_3$OD, 100 MHz): 172.6 (C-2'/5'), 135.3 (C-3'/4'), 104.4 (C-1"), 78.2 (C-3"), 77.9 (C-2"), 75.1 (C-5"), 71.7 (C-10), 70.9 (C-4"), 62.8 (C-6"), 38.5 (C-1), 30.8 (C-2), 30.5 (×3), 30.1, 29.4, 27.7, 27.0 (CH$_2$Alk)

Example 10

Insertion of Maleimide Moiety into Pro-Conjugate for Connection to Albumin Carrier Synthesis of non-cleavable linker pro-conjugate with maleimide moiety 1-[10-(β,D-glucopyranos-1-yl)]-4,11-(diacetic acid)-8-[10-maleimidodecyl]-1,4,8,11-tetraaza cyclotetradecane (39)

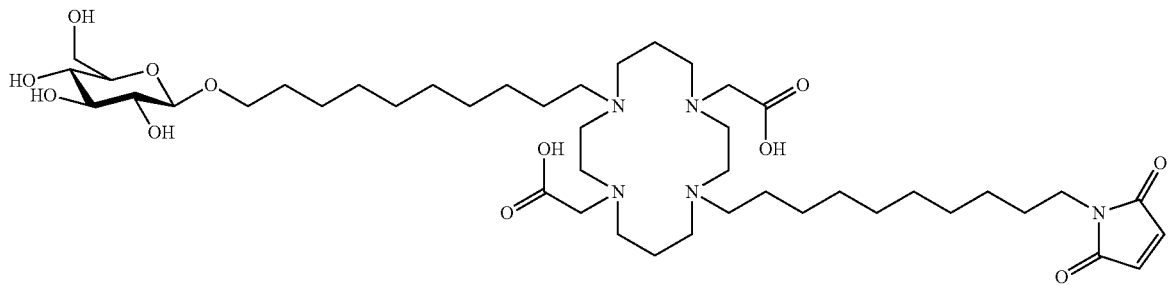

N-(methoxycarbonyl) maleimide (37) (0.008 g, 0.05 mmol) is added at RT to a stirring solution of cyclam 27 (0.015 g, 0.02 mmol) in dioxane (0.75 mL) and sat. NaHCO$_3$ $_{(aq)}$ (1.5 mL). The reaction is stirred for 1 hr after which the reaction is quenched with 0.25 M HCl (5 mL). The aqueous phase is extracted with EtOH:CHCl$_3$ (2:1)(5×5 mL). The organic layers are combined, dried, filtered and the solvent evaporated under vacuum to yield the product as an oil.

Synthesis of Cleavable Linker Pro-Conjugate with Maleimide Moiety

1-[10-(β,D-glucopyranos-1-yl)]-4,11-(diacetic acid)-8-[3-((maleimidodecyl)disulfanyl)propyl]-1,4,8,11-tetraazacyclotetradecane (40)

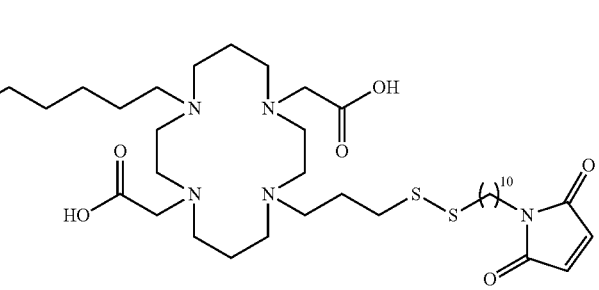

N-(methoxycarbonyl) maleimide (37) (0.008 g, 0.05 mmol) is added at RT to a stirring solution of cyclam 32 (0.015 g, 0.02 mmol) in dioxane (0.75 mL) and sat. NaHCO$_3$ $_{(aq)}$ (1.5 mL). The reaction is stirred for 1 hr after which the reaction is quenched with 0.25 M HCl (5 mL). The aqueous phase is extracted with EtOH:CHCl$_3$ (2:1)(5×5 mL). The organic layers are combined, dried, filtered and the solvent evaporated under vacuum to yield the product as an oil.

1-[10-(β,D-glucopyranos-1-yl)]-4,11-(diacetic acid)-8-[3-((maleimidopropyl-1H-1,2,3-triazol-4-yl)propyl))disulfanyl)propyl]-1,4,8,11-tetraazacyclotetradecane (41)

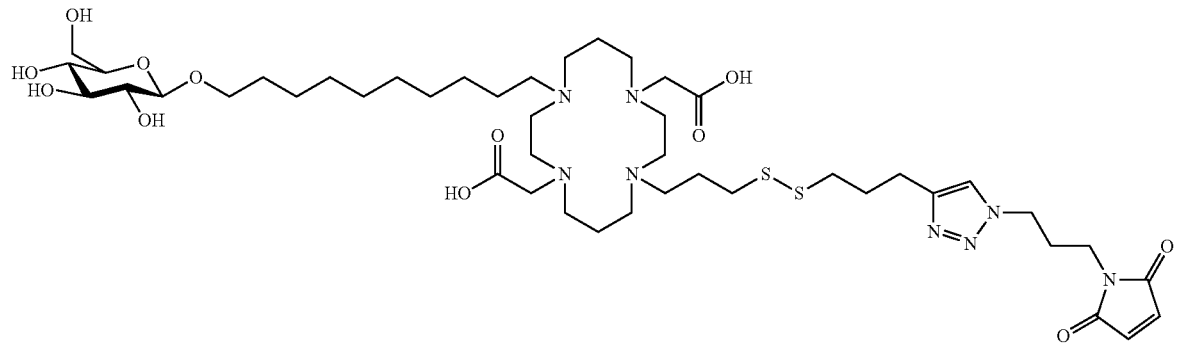

Example 11

Attachment of Maleimido-Functionalised Compounds to Albumin

Reaction of albumin with maleimido-glycoside 38

3-Azidopropyl-1-maleimide (0.002 g, 0.02 mmol) is added at RT to a stirring solution of diisopropyethylamine (0.0013 g, 0.01 mmol), cyclam 33 (0.015 g, 0.02 mmol) and catalytic copper iodide (0.2 eq) in DMF (1.0 mL) The reaction is stirred for 2 hr after which the reaction was quenched with 0.25 M HCl (1 mL). All solvent is evaporated under vacuum and the residue redissolved in 0.25 M HCl (2 ml) followed by extraction of the product with EtOH:CHCl₃ (2:1)(5×3 mL). The organic extracts are combined, dried, filtered and concentrated to yield the title compound.

Control solutions of BSA and 38 were made by dissolving BSA (0.016 g, 0.24 umols) and 38 (0.001 g, 2.4 umols) each in 1×PBS (1 mL). 20 uL of each control solution was analysed by HPLC under a gradient elution with A: CH$_3$CN (0.1% TFA) and B: H$_2$O (0.1% TFA), 0-60% A over 30 min. HPLC analysis was done on an Agilent 1220 Infinity LC with an Agilent Zorbax Eclipse Plus C-18 (4.6×150 mm 5 um) column. The control solutions were then heated at 37° C. for 24 hrs and re-analysed by HPLC using the same method.

Fresh solutions of BSA and 38 were prepared as above and reacted together in an Eppendorf vial by heating at 37° C. After 5 min, a sample of the solution was analysed by HPLC using the same method as above.

Reaction of albumin with maleimido-pro-conjugate 39

Control solutions of BSA and 39 are made by dissolving BSA (0.007 g, 0.11 umols) and 39 (0.001 g, 1.1 umols) each in 1×PBS (1 mL). 20 uL of each control solution was analysed by HPLC under a gradient elution with A: CH$_3$CN (0.1% TFA) and B: H$_2$O (0.1% TFA), 0-60% A over 30 min. HPLC analysis is done on an Agilent 1220 Infinity LC with an Agilent Zorbax Eclipse Plus C-18 (4.6×150 mm 5 um) column. The control solutions are then heated at 37° C. for 24 hrs and re-analysed by HPLC using the same method.

Fresh solutions of BSA and 39 are prepared as above and reacted together in an Eppendorf vial by heating at 37° C. After 5 min, a sample of the solution was analysed by HPLC using the same method as above.

The invention claimed is:

1. A molecule comprising a metabolite that targets tumour cells, a chelating agent capable of containing a radionuclide, and a cleavable linker capable of binding with an EPR agent, or a cleavable linker bound to an EPR agent,
wherein the molecule is a linear molecule comprising, in sequence:
a metabolite that is less than 1000 Da is size and that targets tumour cells, bound to a chelating agent capable of containing a radionuclide, bound to
a) a cleavable linker capable of binding with an EPR agent that is greater than 40 kDa in size or
b) a cleavable linker bound to an EPR agent that is greater than 40 kDa in size,
wherein the cleavable linker contains a cleavable bond that is cleaved in vivo within a tumour environment.

2. The molecule claimed in claim 1, wherein the cleavable bond cleaved in vivo within a tumour environment by a pH of less than 7, by glutathione, or where there is up-regulation of enzymes.

3. The molecule claimed in claim 1, wherein the cleavable linker is bound to the EPR agent.

4. The molecule claimed in claim 1, wherein the cleavable linker comprises a carbon chain of 4 to 20 carbon atoms.

5. The molecule claimed in claim 4, wherein the cleavable linker comprises a carbon chain of 8 to 15 carbon atoms.

6. The molecule claimed in claim 2, wherein the cleavable linker contains a hydrazone bond, a disulfide bond, or enzymatically cleavable peptide sequences.

7. The molecule claimed in claim 3, wherein the EPR agent is selected from polymeric nanoparticles, polymeric micelles, dendrimers, liposomes, viral nanoparticles, carbon nanoparticles, and proteins that accumulate in a tumour in vivo due to the Enhanced Permeability and Retention (EPR) effect.

8. The molecule claimed in claim 7, wherein the EPR agent is a synthetic polymer that is biodegradable, a synthetic polymer that is biocompatible but not biodegradable, or a natural polymer.

9. The molecule claimed in claim 8, wherein the biodegradable synthetic polymer is polyglutamate (PG), polylactide (PLA) or poly(D,L-lactide-co-glycolide)(PLGA).

10. The molecule claimed in claim 8, wherein the polymer that is biocompatible but not biodegradable is Polyethylene glycol (PEG) or N-(2-hydroxypropyl) methylacrylamide (HMPA).

11. The molecule claimed in claim 8, wherein the natural polymer is albumin, chitosan or heparin.

12. The molecule claimed in claim 1, wherein the metabolite that targets tumour cells is 100 to 700 Da in size.

13. The molecule claimed in claim 12, wherein the metabolite that targets tumour cells is folate, mannose, glucose or galactose.

14. The molecule claimed in claim 1, wherein the chelating agent is a cyclic or acyclic bifunctional chelating agent (BFCA) which is able to complex a radioisotope.

15. The molecule claimed in claim 14, wherein the chelating agent is a cyclic chelator selected from: 1,4,7-Triazacyclononane (TACN); 1,4,7-triazacyclononane-triacetic acid (NOTA); 1,4,7-triazacyclononane-N-succinic acid-N',N''-diacetic acid (NOTASA); 1,4,7-triazacyclononane-N-glutamic acid-N',N''-diacetic acid (NODAGA); 1,4,7-triazacyclononane-N,N',N''-tris (methylenephosphonic) (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri (methanephosphonic acid) (DO3P); 1,4,7,10-tetraazacyclodecane-1-glutamic acid-4,7,10-triacetic acid (DOTAGA); 1,4,7,10-tetraazacyclododecane-1-succinic acid-4,7,10-triacetic acid (DOTASA); 1,4,8,11-tetraazacyclotetradecane ([14]aneN4) (cyclam); 1,4,8,12-tetraazacyclopentadecane ([15]aneN4); 1,5,9,13-tetraazacyclohexadecane ([16] aneN4); 1,4-ethano-1,4,8,11-tetraazacyclo-tetradecane (et-cyclam); 1,4,8,11-15-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis(carboxymethyl)-1,4,8,11-tetraazabicyclo[6.6.2]-hexadecane (CB-TE2A); 3,6,10,13,16,19-hexaazabicyclo[6.6.6]icosane (Sar); phthalocyanines and their derivatives; porphyrins and their derivatives.

16. The molecule claimed in claim 14, wherein the chelating agent is an acyclic chelator selected from: ethylene-diamine-tetraacetic-acid (EDTA); and diethylene-tri-amine-penta-acetic acid (DTPA); S-acetylmercaptosuccinic anhydride (SAMSA); (2-mercaptoethyl)(2-((2-mercaptoethyl)amino)ethyl)-carbamic acid (N2S2-DADT); 1,1'-(ethane-1,2-diylbis(azanediyl))bis(2-methylpropane-2-thiol) (N2S2 BAT-TM), (2-(2-mercaptoacetamido)ethyl)-cysteine (N2S2-MAMA); 2,3-bis(2-mercaptoacetamido)-propanoic acid (N2S2 DADS); ethylenedicysteine (EC); 2,2',2"-nitrilotriethanethiol (NS3); 2-ethylthio-N,N-bis(pyridin-2-yl) methyl-ethanamine (N3S); ((2-mercaptoacetyl) glycylglycyl)carbamic acid (MAG3) and 4-(2-(2-(2-mercaptoacetamido)acetamido)-acetamido)butanoic acid (MAG2-GABA); (1,2-bis{[[6-(carboxy)pyridine-2-yl] methyl]-amino}-ethane) (H2dedpa); Nitrilotris(methylene-phosphinic acid) (NTMP); ethylenediaminetetramethylene-phosphonic acid (EDTMP), diethylenetriaminepenta-methylene phosphonic acid (DTPMP); Hydrazinonicotinic acid (HYNIC); N'-{5-[Acetyl(hydroxy)amino]-pentyl}-N-[5-({4-[(5-aminopentyl)-(hydroxy)amino]-4-oxobutanoyl}amino)pentyl]-N-hydroxysuccin-amide (Deferoxamine).

17. The molecule claimed in claim 1, wherein the radionuclide is a radionuclide that may be used for imaging selected from: $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{16}$F, and $^{123}$I.

18. The molecule claimed in claim 1, wherein the radionuclide is a radionuclide that may be used for therapeutic purposes selected from: $^{188}$Re, $^{186}$Re, $^{153}$Sm, $^{166}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{199}$Au, $^{195m}$Pt, $^{193m}$Pt, $^{197}$Pt, $^{117m}$Sn, $^{103}$Pd, $^{103m}$Rh, $^{177}$Lu, $^{223}$Ra, $^{224}$Ra, $^{227}$Th, $^{32}$P, $^{161}$Tb and $^{33}$P, $^{125}$I, $^{203}$Pb, $^{201}$Ti, $^{119}$Sb, $^{58m}$Co, and $^{161}$Ho.

19. The molecule claimed in claim 1, wherein the radionuclide is an Auger electron emitting radionuclide.

20. The molecule claimed in claim 19, wherein the Auger electron emitting radionuclide is selected from $^{111}$In, $^{203}$Pb, $^{201}$Ti, $^{103}$Pd, $^{103m}$Rh, $^{119}$Sb, $^{58m}$Co, $^{161}$Ho, $^{161}$Tb, $^{61}$Cu, $^{67}$Cu, $^{195m}$Pt, $^{193m}$Pt, and $^{117m}$Sn.

21. The molecule claimed in claim 1, wherein the chelating agent contains the radionuclide.

22. The molecule as claimed in claim 1, wherein:
the metabolite that targets tumour cells is a glucose-containing linker that is functionalised for connection to the chelating agent through alkylation or acylation;
the chelating agent is a cyclam functionalised through N-linkages for radioisotope chelation;
the linker is functionalised with maleimide; and
the EPR agent is albumin.

23. The molecule as claimed in claim 22, further comprising $^{103}$Pd.

24. A method for the synthesis of a molecule as defined in claim 1 includes the steps of:
functionalization of a metabolite that targets tumour cells, wherein the metabolite is reacted with an alkyl halide chain to form a metabolite connected to a carbon chain with a terminal functional group that is then converted into a halide or an acid chloride;
functionalization of a cleavable linker, wherein two fragments with terminal functional groups are connected through a bond that can be cleaved, the first fragment containing an alkyl halide at one end for attachment to the chelating agent and a suitable group to form the cleavable bond at the other terminus and the second fragment with a protected amine at the one end and a suitable group to react with the first fragment to form the cleavable bond at the other end;
functionalization of a chelating agent, wherein the chelating agent is first mono-alkylated with the linker and then alkylated a second time with the metabolite, and wherein the remaining amines of the macrocycle are reacted with acetate groups that assist in metal complexation, and wherein the terminal amine is then converted into a functional group capable of binding to an EPR agent.

* * * * *